United States Patent [19]

Yamamura et al.

[11] Patent Number: 5,780,866
[45] Date of Patent: Jul. 14, 1998

[54] METHOD AND APPARATUS FOR AUTOMATIC FOCUSING AND A METHOD AND APPARATUS FOR THREE DIMENSIONAL PROFILE DETECTION

[75] Inventors: Hisae Yamamura; Yukio Matsuyama, both of Yokohama; Takanori Ninomiya, Matoi Hiratsuka; Hideaki Sasazawa, Yokohama, all of Japan

[73] Assignee: Hitachi, Ltd., Tokyo, Japan

[21] Appl. No.: 559,946

[22] Filed: Nov. 17, 1995

[30] Foreign Application Priority Data

Nov. 18, 1994 [JP] Japan .................................. 6-285165
May 9, 1995 [JP] Japan .................................. 7-109856

[51] Int. Cl.$^6$ .............................. G01N 21/84; G01B 11/24
[52] U.S. Cl. .................... 250/559.22; 250/201.4; 356/376
[58] Field of Search ........................ 250/559.22, 201.2, 250/201.4; 356/376

[56] References Cited

U.S. PATENT DOCUMENTS 4,650,333  3/1987  Crabb et al. .................... 356/376
4,677,302  6/1987  Chiu et al. ...................... 250/560
5,103,105  4/1992  Ikegaya et al. .................. 250/561

*Primary Examiner*—Edward P. Westin
*Assistant Examiner*—Kevin Pyo
*Attorney, Agent, or Firm*—Antonelli, Terry, Stout, & Kraus, LLP

[57] ABSTRACT

A method for automatic focusing and three dimensional profile detection and an apparatus for automatic focusing and three dimensional profile detection have the purpose of detecting a three dimensional profile of the state of mounting of parts or soldering on a board without the affects of warp, even if the board of the detection object is warped, as if the surface of the board were on a flat plane. The board surface height is detected in a plurality of windows corresponding to stage scanning regions from a three dimensional profile signal of the part-mounted board detected by a height detection optical system. The board height or inclination in the next window is forecasted from the board surface height and the control history of stage height in the already-detected plurality of windows. Based on the forecasted board surface height or inclination, the speed or height in the Z direction of a Z-stage is controlled according to a feed-forward method with scanning so as that the board surface and the focal plane of the height detection optical system are made coincident.

26 Claims, 12 Drawing Sheets

LEFT-SIDE HALF OF HISTOGRAM

RIGHT-SIDE HALF OF HISTOGRAM

XY STAGE SCANNING

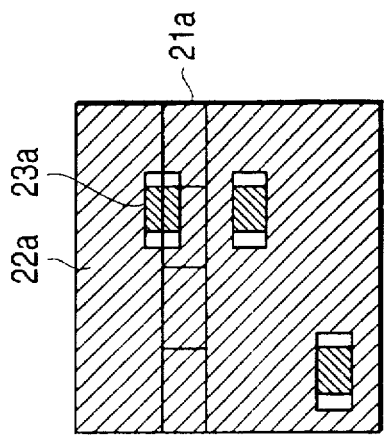
FIG. 13(a)
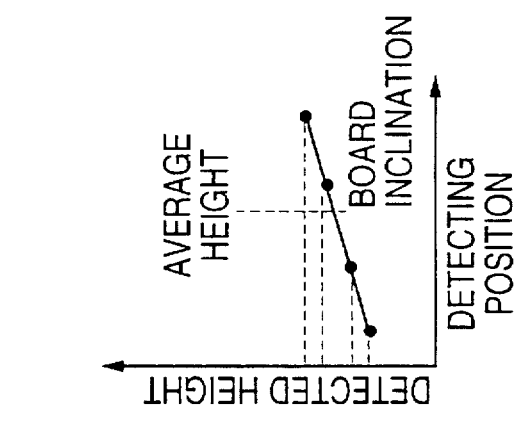
FIG. 13(f)
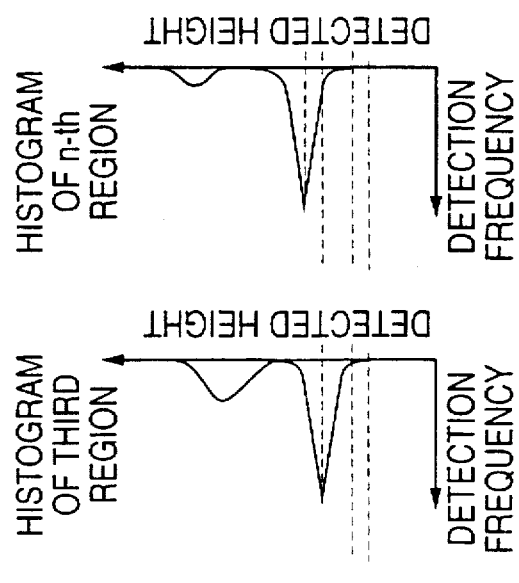
FIG. 13(e)
HISTOGRAM OF n-th REGION
FIG. 13(d)
HISTOGRAM OF THIRD REGION
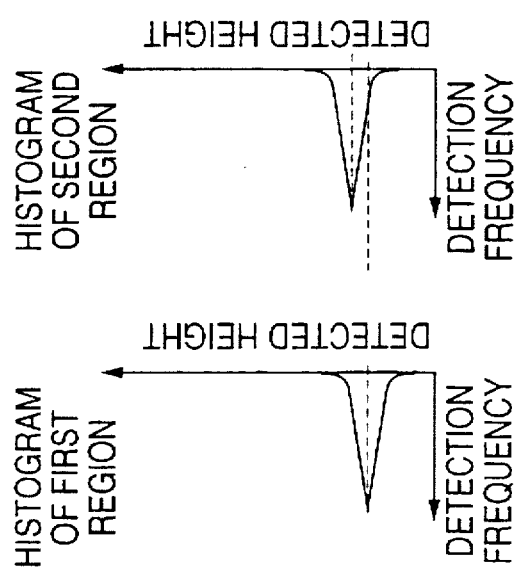
FIG. 13(c)
HISTOGRAM OF SECOND REGION
FIG. 13(b)
HISTOGRAM OF FIRST REGION

METHOD AND APPARATUS FOR AUTOMATIC FOCUSING AND A METHOD AND APPARATUS FOR THREE DIMENSIONAL PROFILE DETECTION

BACKGROUND OF THE INVENTION

This invention relates to a method and apparatus for automatic focusing used for part-mounted board inspection equipment of the type which is able to detect the three dimensional profile of a part-mounted board and to judge whether there is a failure in the mounting of parts and a failure in the soldering, and more particularly to a method and apparatus for automatic focusing, which forecasts the height of a board surface regardless of whether or not the parts are mounted on the region of a part-mounted board having a severe warp, while continuous and high speed scanning is performed, and which automatically controls the focus of the optical system consistently at the forecasted height of the board surface. The invention also relates to a method and apparatus for three dimensional profile detection which is capable of detecting accurately the three dimensional profile of part-mounted boards to detect such problems as failure mounting of parts and failure soldering without being affected by the warp of the board and the part-mounting density.

Conventionally, to inspect the state of electronic parts mounted by soldering on a printed board and the soldering state thereof, automatic inspection optical means, such as cameras and laser devices, have been used. For these part-mounted board inspection devices, means which detect the three dimensional profile of a mounted board and judge defects by image processing have been often used. In this case, it is necessary to detect the height of a board as a reference to judge the state of soldering based on a detected three dimensional profile.

Conventionally, to detect a change of board height due to warping of the board to be inspected, methods in which the height of the board surface is detected in a detected image and the position of parts and the height of parts are detected, referring to the detected height of the board surface, have been known.

In detail, in the prior art-1 (Japanese Patent Laid-Open No. Hei 3-188306 (1991)) shown in FIG. 15(a), there is described an inspection device for inspecting the appearance of mounted boards in which a plurality of windows are provided for inspecting one part, and in which, from a histogram of detected height in the windows a board height in each window is detected, as shown in FIG. 15(b) so that failures, such as unintended angular and positional discrepancies can be detected.

In another prior art-2 (Japanese Patent Laid-Open No. Hei 4-208803 (1992)), a method is described in which, referring to three point heights where no part is mounted, the board inclination is detected.

In the prior art-3 (Japanese Patent Laid-Open No. Hei 4-369411 (1992)), a method is described in which a histogram of the height near mounted parts is obtained, and the profile of a solder connection is measured with reference to the centroid position of peaks in the histogram as a reference height.

In the prior art-4 (Japanese Patent Laid-Open Hei 2-8706 (1990)), a method is described in which a light beam is irradiated on the surface of a measurement object, the position of the reflected light spot is detected to detect a height signal, and the position of the optical sensor for detecting height is controlled depending on the detected height, the height of an object can be measured in a high resolution range of a height detector.

In the prior art-5 (Japanese Patent Laid-Open No. Hei 4-289408 (1992)) shown in FIG. 16, a wiring pattern detector is described in which a laser beam is irradiated from an inclined direction onto a warped board, and the reflected light is inputted to a position detecting element to detect the height of an inspection object.

In the prior art-6 (Japanese Patent Laid-Open No. Sho 62-31815 (1987)), a method is described in which a stripe pattern is projected on the surface of an LSI wafer, the contrast of the projected stripe pattern is detected to detect the focal position, and thus focusing is completed.

Generally, a height detector with high resolution is required to precisely detect a small object, such as a solder profile, however, usually the detectable height range (depth of focus) of such detector is narrow. Therefore, the methods described in prior art-2 and prior art-3, which have no automatic focusing, can not detect the image when the height of the whole board changes due to warping of an inspection object and the change results in protrusion of the soldering part outside the inspectable range. This is a serious disadvantage of these methods.

The conventional method of focusing as described in prior art-4 consumes a long time when a wide region of a board is inspected, because the height detection is carried out by spot detection, which is a serious disadvantage of this method.

The wiring pattern detector described in prior art-5 can not detect the height accurately on a region where parts are mounted, therefore this apparatus can not be used for part-mounted boards. Another disadvantage is the requirement of a height detector in addition to the three dimensional profile detector.

In the case of the method of automatic focusing described in prior art-6, when it is applied to part-mounted boards, the height of a board surface is detected accurately on a region where no part is mounted, however, on a region where parts cover a significant portion of the board surface and only a small detectable board surface, the detector may erroneously miss-detect the part surface for the board height, which is a serious disadvantage of this detector.

SUMMARY OF THE INVENTION

It is an object of the present invention to provide a method and apparatus for automatic focusing which will forecast the height of a board surface in the next scanning region, while high speed continuous scanning is carried out, regardless of the existence of parts mounted on the board (regardless of a part-mounted region or not), will automatically focus the detector at the forecasted height of the board surface, and will detect a three dimensional (abbreviated as 3D hereinafter) profile of the state of mounting of parts or a three dimensional profile of the state of soldering as if the board surface were laid on a flat plane without being affected by warp, if the board having mounted parts to be detected is warped, whereby the present invention is able solve the above-mentioned disadvantages of the prior art.

It is a further object of the present invention to provide a method and apparatus for detecting a 3D profile which will consistently focus the detector on a board surface, while high speed continuous scanning is carried out, regardless of the existence of parts mounted on the board (regardless of a part-mounted region or not), and will detect the profile as if the board surface were on a flat plane without being affected by warp, if the board having mounted parts to be detected is warped.

It is yet another object of the present invention to provide a method and apparatus for inspecting part-mounted boards which will consistently focus the detector on a board surface, while performing high speed continuous scanning, regardless of the existence of parts mounted on the board (regardless of a part-mounted region or not), and will inspect the state of mounting or the state of bonding of parts mounted on the board without being affected by warp, if the board having mounted parts to be detected is warped.

To accomplish the above-mentioned objects, the present invention provides an automatic focusing method for a height detection optical system, in which a stage scanning region is set on a part-mounted board supported on the stage and a three dimensional profile of the part-mounted board is detected by scanning the stage scanning region, wherein the board surface height in a plurality of windows, which is set corresponding to the stage scanning region, is detected from a three dimensional profile signal of the part-mounted board; the board surface height or inclination in the next window is forecasted from the board surface height in an already detected plurality of windows and the control history of stage height; and the speed or the height of the Z-stage in the Z direction is controlled while the scanning is performed so that the board surface is made to coincide with the focal plane of the height detection optical system based on the forecasted board surface height or inclination according to a feedforward method.

In the above-mentioned automatic focusing method, depending on whether a forecast of the board surface height or inclination in the next window is valid or invalid, when histograms of a three dimensional signal are calculated for each window, the board surface height of the window is detected from the corresponding histogram, and when the difference between the detected board surface height and the focal plane of the height detection optical system is within a certain prescribed range so that the detected board height is judged to be valid, the board surface height or inclination in the window to be scanned next is forecasted from the already detected board surface height in a plurality of windows, including the windows detected for a histogram and the control history of the stage height. On the other hand, when the above-mentioned difference is not in a certain prescribed range so that the detected board height is judged to be invalid, the board surface height or inclination in the window to be scanned next is forecasted from the already detected board height in a plurality of windows not including the windows detected for the histogram.

In the above-mentioned automatic focusing method, the plurality of windows not including the windows for a histogram to be used when the difference is not in a certain prescribed range and the detected board height is judged to be invalid include the newest window where the valid board height has been detected, a window adjacent to the newest window on the immediately preceding page where the valid board height has been detected, and a window adjacent to the window to be scanned just after the addressed window on the immediately preceding page where the valid board height has been detected.

The present invention provides an automatic focusing apparatus, in which a stage scanning region is set on a part-mounted board supported on the stage and a three dimensional profile of the part-mounted board is detected by scanning the stage scanning region, wherein the automatic focusing apparatus is provided with a control means for scan-controlling the stage two-dimensionally, a board height detection means for detecting and memorizing the board surface height in a plurality of windows which are set on a stage scanning region which is scanning-controlled by the control means from a three dimensional profile signal of the part-mounted board detected by the height detection optical system, a board height forecasting means for forecasting the board surface height or inclination in the next window based on the board surface height in a plurality of windows which are detected and memorized by the board height detection means, and a stage height control means for controlling the speed or height of the Z-stage in the Z-direction according to a feedforward method, so as that the board surface and the focal plane of the height detection optical system are made coincident based on the board surface height or inclination in the next window as forecasted by the board height forecasting means.

The present invention provides a three dimensional profile detection method, in which a height detection optical system detects a three dimensional image signal from a part-mounted board by scanning two-dimensionally the part-mounted board; the board surface height is detected for each desired region from the detected three dimensional profile image signal; and, based on the detected board surface height, the distance between the height detection optical system and the board is controlled, and a three dimensional profile image signal of the part-mounted board is detected by the height detection optical system from the scanning region adjacent to the desired region.

The present invention provides a three dimensional profile detection method, in which a height detection optical system detects a three dimensional image signal from a part-mounted board by scanning two-dimensionally the part-mounted board; the board surface height is detected for each desired region from the detected three dimensional profile image signal; and, based on the detected board surface height, a three dimensional profile image signal of the part-mounted board is detected by the height detection optical system from the scanning region adjacent to the desired region.

The present invention provides a three dimensional profile detection method, in which a height detection optical system detects a three dimensional image signal from a part-mounted board by scanning two-dimensionally the part-mounted board; from the detected three dimensional profile image signal, a frequency distribution of the board surface height is prepared for each desired scanning region; and, in the prepared frequency distribution of the board surface height, when the detected frequency is a certain prescribed threshold value Fth or higher and the detected value representing the board surface height lies in a range of $H_0 \pm \alpha$, $H_0$ representing a standard height and $\alpha$ representing a prescribed range, based on the value representing the board surface height obtained as a valid board surface height, the distance between the height detection optical system and the board is controlled and a three dimensional profile image signal of the part-mounted board is detected by the height detection optical system from the scanning region adjacent to the desired scanning region.

The present invention provides a three dimensional profile detection method, in which a height detection optical system detects a three dimensional image signal from a part-mounted board by scanning two-dimensionally the part-mounted board; from the detected three dimensional profile image signal, a frequency distribution of the board surface height is prepared for each desired scanning region; and, in the prepared frequency distribution of the board surface height, when the detected frequency is a certain prescribed threshold value Fth or higher and the detected value representing the board surface height lies in a range of $H_0 \pm \alpha$, $H_0$ representing a standard height and α representing a prescribed range, based on the value representing the board surface height obtained as a valid board surface height, the three dimensional profile image signal of the part-mounted board detected by the height detection optical system from the scanning region adjacent to the desired scanning region is corrected, and the three dimensional profile signal is detected.

The present invention provides a three dimensional profile detection method, in which a height detection optical system detects a three dimensional image signal from a part-mounted board by scanning two-dimensionally the part-mounted board; from the detected three dimensional profile image signal, a frequency distribution of the board surface height is prepared for each desired scanning region; and, in the prepared frequency distribution of the board surface height, when the detected frequency is a certain prescribed threshold value Fth or higher and the detected value representing the board surface height lies in a range of $H_0 \pm \alpha$, $H_0$ representing a standard height and α representing a prescribed range, the value representing the board surface height obtained as a valid board surface height is averaged for the adjacent scanning region, the distance between the height detection optical system and the board is controlled based on the value which represents the average board surface height, and a three dimensional profile image signal of the part-mounted board is detected by the height detection optical system from the scanning region adjacent to the desired scanning region.

The present invention provides a three dimensional profile detection method, in which a height detection optical system detects a three dimensional image signal from a part-mounted board by scanning two-dimensionally the part-mounted board; from the detected three dimensional profile image signal, a frequency distribution of the board surface height is prepared for each desired scanning region; and, in the prepared frequency distribution of the board surface height, when the detected frequency is a certain prescribed threshold value Fth or higher and the detected value representing the board surface height lies in a range of $H_0 \pm \alpha$, $H_0$ representing a standard height and α representing a prescribed range, the value representing the board surface height obtained as a valid board surface height is averaged for the adjacent scanning region, the three dimensional profile image signal of the part-mounted board detected by the height detection optical system from the scanning region adjacent to the desired scanning region is corrected based on the value which represents the average board surface height, and the three dimensional profile signal is detected.

The present invention provides a three dimensional profile detection method, in which a height detection optical system detects a three dimensional image signal from a part-mounted board by scanning two-dimensionally the part-mounted board; from the detected three dimensional profile image signal, a frequency distribution of the board surface height is prepared for each desired scanning region; in the prepared frequency distribution of the board surface height, when the detected frequency is a certain prescribed threshold value Fth or higher and the detected value representing the board surface height lies in a range of $H_0 \pm \alpha$, $H_0$ representing a standard height and α representing a prescribed range, based on the value representing the board surface height obtained as a valid board surface height, the distance between the height detection optical system and the board is controlled; and, in the prepared frequency distribution of the board surface height, when the detected frequency is not a certain prescribed threshold value Fth or higher, or the detected frequency is a certain prescribed threshold value Fth or higher and the detected value representing the board surface height does not lie in a range of $H_0 \pm \alpha$, the distance between the height detection optical system and the board is controlled based on the value which represents the already detected valid board surface height in the neighboring scanning region as the invalid board surface height, and a three dimensional profile image signal of the part-mounted board is detected by the height detection optical system from the scanning region adjacent to the desired scanning region.

The present invention provides a three dimensional profile detection method, in which a height detection optical system detects a three dimensional image signal from a part-mounted board by scanning two-dimensionally the part-mounted board; from the detected three dimensional profile image signal, a frequency distribution of the board surface height is prepared for each desired scanning region; in the prepared frequency distribution of the board surface height, when the detected frequency is a certain prescribed threshold value Fth or higher and the detected value representing the board surface height lies in a range of $H_0 \pm \alpha$, $H_0$ representing a standard height and α representing a prescribed range, the value representing the board surface height obtained as a valid board surface height is averaged for the adjacent scanning region; based on the value which represents the averaged board surface height, the three dimensional profile image signal of the part-mounted board detected by the height detection optical system from the scanning region adjacent to the desired scanning region is corrected; and, in the prepared frequency distribution of the board surface height, when the detected frequency is not a certain prescribed threshold value Fth or higher, or the detected frequency is a certain prescribed threshold value Fth or higher and the detected value representing the board surface height does not lie in a range of $H_0 \pm \alpha$, then based on the value which represents the already detected valid board surface height in the neighboring scanning region as the invalid board surface height, the three dimensional profile image signal of the part-mounted board detected by the height detection optical system from the scanning region adjacent to the desired scanning region is corrected, and the corrected three dimensional profile signal is detected.

The present invention provides a three dimensional profile detection method, in which a part-mounted board is scanned two-dimensionally, thereby, a three dimensional profile image is detected by a height detection optical system; the board surface height is detected for each divided region, which represents the detected three dimensional profile divided to a certain prescribed size; the validity of the detected board surface is judged; then, based on the board height judged to be valid, the distance between the height detection optical system and the board surface is controlled; and the three dimensional profile image signal is detected.

The present invention provides a three dimensional profile detection apparatus, which includes a height detection optical system for scanning two-dimensionally a part-mounted board to detect a three dimensional profile image signal from the part-mounted board, and a board height detecting and controlling means for detecting the board surface height for each desired scanning region from the three dimensional profile signal detected by the height detection optical system, and for controlling the distance between the height detection optical system and the board to detect, using the height detection optical system, the three dimensional image signal of the part-mounted board from the scanning region adjacent to the desired scanning region based on the detected board surface height.

The present invention provides a three dimensional profile detection apparatus, including a height detection optical system for scanning two-dimensionally a part-mounted board to detect a three dimensional profile image signal from the part-mounted board, and a board height detecting and correcting means for detecting the board surface height for each desired scanning region from the three dimensional profile signal detected by the height detection optical system, for correcting the three dimensional profile image signal of the part-mounted board detected by the height detection optical system from the scanning region adjacent to the desired scanning region based on the detected board surface height, and for detecting the three dimensional profile signal.

The present invention provides a three dimensional profile detection apparatus, including a height detection optical system for scanning two-dimensionally a part-mounted board to detect a three dimensional profile image signal from the part-mounted board, and a board height detecting and controlling means for preparing the frequency distribution of the board surface height for each desired scanning region from the three dimensional profile signal detected by the height detection optical system, in the prepared frequency distribution of the board surface height, when the detected frequency is a certain prescribed threshold value Fth or higher and the detected value representing the board surface height lies in a range of $H_0 \pm \alpha$, $H_0$ representing a standard height and $\alpha$ representing a prescribed range, for controlling the distance between the height detection optical system and the board based on the value representing the board surface height obtained as a valid board surface height, and for detecting a three dimensional profile image signal of the part-mounted board by the height detection optical system from the scanning region adjacent to the desired scanning region.

The present invention provides a three dimensional profile detection apparatus, including a height detection optical system for scanning two-dimensionally a part-mounted board to detect a three dimensional profile image signal from the part-mounted board, and a board height detecting and correcting means for preparing a frequency distribution of the board surface height for each desired scanning region from the three dimensional profile signal detected by the height detection optical system, in the prepared frequency distribution of the board surface height, when the detected frequency is a certain prescribed threshold value Fth or higher and the detected value representing the board surface height lies in a range of $H_0 \pm \alpha$, $H_0$ representing a standard height and $\alpha$ representing a prescribed range, for correcting the three dimensional profile image signal of the part-mounted board detected by the height detection optical system from the scanning region adjacent to the desired scanning region based on the value representing the board surface height obtained as a valid board surface height, and for detecting the three dimensional profile signal.

The present invention provides a three dimensional profile detection apparatus, including a height detection optical system for scanning two-dimensionally a part-mounted board to detect a three dimensional profile image signal from the part-mounted board, and a board height detecting and controlling means for preparing a frequency distribution of the board surface height for each desired scanning region from the three dimensional profile signal detected by the height detection optical system, in the prepared frequency distribution of the board surface height, when the detected frequency is a certain prescribed threshold value Fth or higher and the detected value representing the board surface height lies in a range of $H_0 \pm \alpha$, $H_0$ representing a standard height and $\alpha$ representing a prescribed range, for averaging the value representing the board surface height obtained as a valid board surface height for the adjacent scanning region, for controlling the distance between the height detection optical system and the board based on the value which represents the averaged board surface height, and for detecting a three dimensional profile image signal of the part-mounted board by the height detection optical system from the scanning region adjacent to the desired scanning region.

The present invention provides a three dimensional profile detection apparatus, including a height detection optical system for scanning two-dimensionally a part-mounted board to detect a three dimensional profile image signal from the part-mounted board, and a board height detecting and correcting means for preparing a frequency distribution of the board surface height for each desired scanning region from the three dimensional profile signal detected by the height detection optical system, in the prepared frequency distribution of the board surface height, when the detected frequency is a certain prescribed threshold value Fth or higher and the detected value representing the board surface height lies in a range of $H_0 \pm \alpha$, $H_0$ representing a standard height and $\alpha$ representing a prescribed range, for averaging the value representing the board surface height obtained as a valid board surface height for the adjacent scanning region, for correcting the three dimensional profile image signal of the part-mounted board detected by the height detection optical system from the scanning region adjacent to the desired scanning region based on the value which represents the averaged board surface height, and for detecting the three dimensional profile signal.

The present invention provides a three dimensional profile detection apparatus, including a height detection optical system for scanning two-dimensionally a part-mounted board to detect a three dimensional profile image signal from the part-mounted board, and a board height detecting and controlling means for preparing a frequency distribution of the board surface height for each desired scanning region from the three dimensional profile signal detected by the height detection optical system, in the prepared frequency distribution of the board surface height, when the detected frequency is a certain prescribed threshold value Fth or higher and the detected value representing the board surface height lies in a range of $H_0 \pm \alpha$, $H_0$ representing a standard height and $\alpha$ representing a prescribed range, the distance between the height detection optical system and the board is controlled based on the value representing the board surface height obtained as a valid board surface height, in the prepared frequency distribution of the board surface height, when the detected frequency is not a certain prescribed threshold value Fth or higher, or the detected frequency is a certain prescribed threshold value Fth or higher and the detected value representing the board surface height does not lie in a range of $H_0 \pm \alpha$, for controlling the distance between the height detection optical system and the board based on a value which represents the already detected valid board surface height in the neighboring scanning region as the invalid board surface height, and for detecting a three dimensional profile image signal of the part-mounted board by the height detection optical system from the scanning region adjacent to the desired scanning region.

The present invention provides a three dimensional profile detection apparatus, including a height detection optical system for scanning two-dimensionally a part-mounted board to detect a three dimensional profile image signal from the part-mounted board, and a board height detecting and correcting means for preparing a frequency distribution of the board surface height for each desired scanning region from the three dimensional profile signal detected by the height detection optical system, in the prepared frequency distribution of the board surface height, when the detected frequency is a certain prescribed threshold value Fth or higher and the detected value representing the board surface height lies in a range of $H_0 \pm \alpha$, $H_0$ representing a standard height and $\alpha$ representing a prescribed range, for averaging the value representing the board surface height obtained as a valid board surface height for the adjacent scanning region, for correcting the three dimensional profile image signal of the part-mounted board detected by the height detection optical system from the scanning region adjacent to the desired scanning region based on the value which represents the averaged board surface height, in the prepared frequency distribution of the board surface height, when the detected frequency is not a certain prescribed threshold value Fth or higher, or the detected frequency is a certain prescribed threshold value Fth or higher and the detected value representing the board surface height does not lie in a range of $H_0 \pm \alpha$, for correcting the three dimensional profile image signal of the part-mounted board detected by the height detection optical system from the scanning region adjacent to the desired scanning region based on the value which represents the already detected valid board surface height in the neighboring scanning region as the invalid board surface height, and for detecting the corrected three dimensional profile signal.

The present invention provides a three dimensional profile detection apparatus, including a height detection optical system for detecting a three dimensional profile image by scanning a part-mounted board two-dimensionally, and a board height detection and control means for detecting the board surface height for each divided region which represents a detected three dimensional profile divided into a certain prescribed size, for judging the validity of the detected board surface, for controlling the distance between the height detection optical system and the board surface based on the board height judged to be valid, and for detecting the three dimensional profile image signal.

The present invention provides an inspection method for a part-mounted board, in which a height detection optical system detects a three dimensional image signal from a part-mounted board by scanning two-dimensionally the part-mounted board; from the detected three dimensional profile image signal, a frequency distribution of the board surface height is prepared for each desired scanning region, in the prepared frequency distribution of the board surface height, when the detected frequency is a certain prescribed threshold value Fth or higher and the detected value representing the board surface height lies in a range of $H_0 \pm \alpha$, $H_0$ representing a standard height and $\alpha$ representing a prescribed range, then based on the value representing the board surface height obtained as a valid board surface height, the distance between the height detection optical system and the board is controlled; and, based on a three dimensional profile image signal obtained from the part-mounted board by the height detection optical system from the scanning region adjacent to the desired scanning region, the state of mounting of parts or jointing on the board is inspected.

The present invention provides an inspection method for part-mounted board, in which a height detection optical system detects a three dimensional image signal from a part-mounted board by scanning two-dimensionally the part-mounted board; from the detected three dimensional profile image signal, a frequency distribution of the board surface height is prepared for each desired scanning region, in the prepared frequency distribution of the board surface height, when the detected frequency is a certain prescribed threshold value Fth or higher and the detected value representing the board surface height lies in a range of $H_0 \pm \alpha$, $H_0$ representing a standard height and $\alpha$ representing a prescribed range; then, based on the value representing the board surface height obtained as a valid board surface height, the three dimensional profile image signal of the part-mounted board detected by the height detection optical system from the scanning region adjacent to the desired scanning region is corrected; and, based on the corrected three dimensional profile signal, the state of mounting of parts and jointing on the board is inspected.

The present invention provides a part-mounted board inspecting apparatus, including a height detection optical system for scanning two-dimensionally a part-mounted board to detect a three dimensional profile image signal from the part-mounted board, a board height detecting and controlling means for preparing a frequency distribution of the board surface height for each desired scanning region from the three dimensional profile signal detected by the height detection optical system, in the prepared frequency distribution of the board surface height when the detected frequency is a certain prescribed threshold value Fth or higher and the detected value representing the board surface height lies in a range of $H_0 \pm \alpha$, $H_0$ representing a standard height and $\alpha$ representing a prescribed range, for controlling the distance between the height detection optical system and the board based on the value representing the board surface height obtained as a valid board surface height, and for detecting a three dimensional profile image signal of the part-mounted board by the height detection optical system from the scanning region adjacent to the desired scanning region, and an inspecting means for inspecting the state of mounting of parts or jointing on the board based on the three dimensional profile image signal detected from the height detecting and controlling means.

The present invention provides a part-mounted board inspecting apparatus, including a height detection optical system for scanning two-dimensionally a part-mounted board to detect a three dimensional profile image signal from the part-mounted board, a board height detecting and correcting means for preparing a frequency distribution of the board surface height for each desired scanning region from the three dimensional profile signal detected by the height detection optical system, in the prepared frequency distribution of the board surface height, when the detected frequency is a certain prescribed threshold value Fth or higher and the detected value representing the board surface height lies in a range of $H_0 \pm \alpha$, $H_0$ representing a standard height and $\alpha$ representing a prescribed range, for correcting the three dimensional profile image signal of the part-mounted board detected by the height detection optical system from the scanning region adjacent to the desired scanning region based on the value representing the board surface height obtained as a valid board surface height, and an inspecting means for inspecting the state of mounting of parts and jointing on the board based on the three dimensional profile image signal detected from the board height detecting and correcting means.

The present invention provides a method for detecting a three dimensional profile image of the whole area of the part-mounted board by scanning two-dimensionally the part-mounted board using a height detection means for detecting the height of an object by measuring optically the distance to the object, and the method is structured so that, regardless of whether parts are mounted on the board or not, the board surface height is detected continuously synchronism with the image detection for each certain region from the three dimensional profile image, and the distance between the height detection means and the part-mounted board surface is controlled continuously in synchronism with the image detection based on the detected board surface height, thereby, even if the warped part-mounted board is detected, the three dimensional profile image is detected without regard to any warp, as if the board surface were on a flat plane.

The present invention provides a method for detecting a three dimensional profile image of the whole area of the part-mounted board by scanning two-dimensionally the part-mounted board using a height detection means for detecting the height of an object by measuring optically the distance to the object, and the method is structured so that, regardless of whether parts are mounted on the board or not, the board surface height is detected continuously synchronism with the image detection for each certain region from the three dimensional profile image, and the image is corrected in synchronism with the image detection based on the detected board surface height so that the board surface height detected in the three dimensional profile image is kept at a constant value, thereby, even if the warped part-mounted board is detected, the three dimensional profile image is detected without regard to any warp, as if the board surface were on a flat plane.

The present invention has preferably a structure in which, when the board surface height in a certain region is detected, the region is divided into a plurality of sub-regions, and the average of the board surface height obtained by averaging for sub-regions is assigned as the board surface height of the region.

The present invention has preferably a structure in which, with respect to the method for detecting the board surface height in the above-mentioned sub-region, a histogram of height in the region is calculated, and the board surface height of the region is detected based on the frequency peak value of the obtained histogram.

The present invention has preferably a structure in which, in the board surface height detection method using a histogram, the board height to be an originally true or ideal board height out of the part of the histogram having a frequency exceeding a threshold value, which is determined previously from the region, is assigned as a standard value, and the detected height of the highest frequency in the range having a prescribed plus minus error range with a center at the standard value is detected as the board height in the region.

The present invention has preferably a structure in which, in the board surface height detection method using a histogram, when the valid board surface height is not obtained, the board surface height in the region is obtained by extrapolation using the valid board surface height detected in other regions.

By structuring the method as described above, the board surface height is detected on the portion where no part is mounted from a three dimensional profile signal of the board detected on the part-mounted board, and the board surface height or inclination in the portion to be inspected next is determined from the already detected board surface height and control history of the stage height. It is known empirically that the board surface height does not change suddenly because of its rigidity, the forecasting is based on this precondition.

Also, it is known that the board surface of a region, where large parts, such as QFP, are mounted, does not change suddenly because of the rigidity of the parts and is kept flat, based on this precondition, and so the board surface height or inclination in the portion to be inspected next can be forecasted from the board surface height detected around the parts and the control history of the stage height.

The stage height is controlled according to a feedforward method based on the forecasted board surface height or inclination; therefore, the board surface is focussed consistently, as shown in FIG. 9, regardless of whether parts are mounted on the board or not. Therefore, the boundaries of mounted parts are also focussed without deviation, as shown by lines 171 and 181 (focal point of the detection system) in FIG. 17 and FIG. 18, and so the three dimensional profile of soldered portions formed near the board surface can be detected accurately at a high speed.

The feedback system for feedback of the deviation between the board surface height of an object, including its parts, and the focal position of the optical system is used to eliminate the delay, and therefore, a continuous and high speed scanning is possible.

In the case in which four sides of a mounted part (for example QFP (quad flat package: a flat package having leads 193 in four directions) 192 represents a body and 191 represents a substrate) as shown in FIGS. 19(a) and 19(b) with leads 193 to be inspected respectively, the board surface can be focussed consistently, as shown in FIG. 9, and therefore, the three dimensional profile of soldering portion B of the leads 193 can be detected accurately.

By structuring the method as described above, the board surface height is detected continuously in synchronism with the image detection, and based on the detected board surface height, the distance between the height detector and the board surface is controlled continuously; thereby, while continuous and high speed scanning on the board of the inspection object on which surface the focal position of the detector is coincident consistently, as shown in FIG. 9, regardless of whether parts are mounted on the board, without regard to any warp, even if the part-mounted board of the detection object is warped, the detection is possible as if the board surface were laid on a flat plane.

In the case in which four sides of a mounted part 193 have leads 193 to be inspected, by structuring the method as described above, the focal position of the detector can be coincident on the board surface consistently, and therefore, lead portion 193 of the part sides (plane perpendicular to the scanning direction) is detected accurately.

In the case in which the depth of focus of the detection optical system is sufficiently large for the warp of the board of the inspection object, the three dimensional profile image is corrected based on the detected board surface height, so that the board surface height in the three dimensional profile image is kept at a constant value, thereby, the detection is possible without regard to any warp, even if the part-mounted board of the detection object is warped.

According to the present invention, the board surface height is detected continuously and selectively regardless of whether parts are mounted on the board; the distance between the detection optical system and the surface of the board itself is controlled continuously based on the surface height of the detected board itself; and thereby, even if the board is warped, the 3D profile image signal of a part-mounted board can be detected without regard to any warp, as if the surface of the board itself were laid on a flat plane. As a result, the present invention exhibits the effect that the state of the part mounting or jointing an be inspected reliably.

According to the present invention, the board surface height is detected continuously and selectively regardless of whether parts are mounted on a board; an image is corrected so as that the board surface height is maintained at a constant value in the 3D profile image based on the surface height of the detected board itself; and thereby, even if the board is warped, the 3D profile image signal of a part-mounted board can be detected without regard to any warp, as if the surface of the board itself were laid on a flat plane. As a result, the present invention exhibits the effect that the state of the part mounting or jointing can be inspected reliably.

According to the present invention, the above-mentioned effect is exhibited without position data for the mounted parts by judging the validity of the detected board height.

According to the present invention, when the method is applied to a part-mounted board inspection apparatus, a 3D profile image signal at joints, such as solder joints on the surface of the board, can be detected accurately by the surface height of the board itself coincident with the focal plane of the detection optical system, whereby the present invention exhibits the effect that the state of part mounting or jointing can be inspected reliably.

According to the present invention, the board surface height is forecasted regardless whether a scanned region is a part-mounted region or not, while a significantly warped part-mounted board is scanned continuously at a high speed, and the optical system is focused automatically at the forecasted board surface height consistently, so that the present invention exhibits the effect that the state of part mounting or jointing an be inspected reliably.

BRIEF DESCRIPTION OF THE DRAWINGS

FIGS. 13(a) through 13(f) are diagrams for describing another board height detection method using the board height detection part shown in FIG. 1 and FIG. 10 as shown in FIG. 4;

DESCRIPTION OF THE PREFERRED EMBODIMENTS

Figure 1:
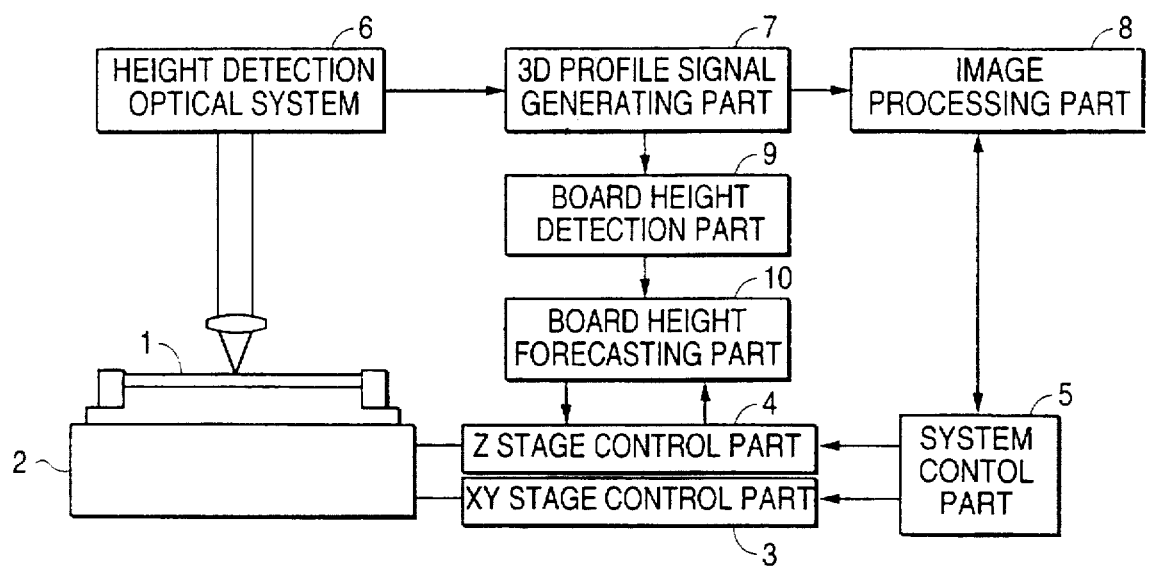
FIG. 1 is a block diagram for illustrating the integrated structure of one embodiment of an image processing device for processing image signals involving a 3D profile of a part-mounted board in accordance with the present invention.

Embodiments of the present invention will be described in detail with reference to FIG. 1 to FIG. 9.

In the description of this embodiment, a region which is being detected while the stage travels a certain distance on an inspection object, namely a certain region of a stage during scanning, is referred to as a window, and one series of stages during scanning, namely a region detected by a series of windows, is referred to as a page.

A part-mounted board 1, which is the inspection object (referred simply as a board), is supported on an XYZ-stage 2. The XYZ-stage 2 is controlled by an XY-stage control part 3 and a Z-stage control part 4. A system control part 5 feeds XY-stage data, generated the basis of on design data, to the XY-stage control part 3. A height detection optical system 6 is provided for detecting the surface height of the board 1. A 3D profile signal generation part 7 receives surface height data relating to the board 1 from the height detection optical system 6, and generates a 3D profile signal of the board 1. An image processing part 8 image-processes the 3D profile signal and detects any defect. A board height detection part 9 detects surface height data relating to the board 1 for each window, and sends the detected height data to a board height forecasting part 10. The board height forecasting part 10 forecasts the surface height or inclination of the board 1 in the next window based on the surface height data and stage height data for the board 1; and, based on the forecast, the part 10 generates height control data so that the surface of the board 1 is made coincident with the focal plane of the detection optical system 6, and then feeds it to the Z-stage control part 4.

The height detection optical system 6 will be described with reference to FIG. 2.

Both optical axes of a Fourier transformation lens 12 and another Fourier transformation lens 13 are disposed on the same plane perpendicular to the axis of rotation of a light beam deflector 14, and are provided so as to cross each other on the light beam deflector 14. A laser beam source 11 and a photoelectric converter 17 are provided on the object plane of the Fourier transformation lens 12. The axis of rotation of the light beam deflector 14 is provided on the Fourier transformation planes of the two Fourier transformation lenses 12 and 13. The laser beam irradiated from the laser beam source 11 is transformed by the Fourier transformation lens 12, and becomes a light flux crossing with the optical axis of the Fourier transformation lens 12 with an angle at the light beam deflector 14. Then, the light flux reflected on the light beam deflector 14 is reverse-Fourier-transformed by the Fourier transformation lens 13 and projects a laser spot on an inspection object through a reflecting mirror 15. This laser spot moves in a direction perpendicular to the optical axis of the Fourier transformation lens 13 on the inspection object as the light beam deflector 14 rotates, and, because of the change in direction of the light flux from the light beam deflector 14, for example from A to B, this motion of the laser spot can be utilized in scanning.

On the other hand, for the detecting side, the laser spot enters into the Fourier transformation lens 13, as shown with a rough dotted line with an arrow head, through a reflecting mirror 16, and forms a Fourier transformed image on the light beam deflector. The Fourier transformed image is reflected by the light beam deflector 14, is reverse-Fourier-transformed by the Fourier transformation lens 12, and forms a real image of the laser spot on the photoelectric converter 17. As shown with a Z-arrow, when the height of the inspection object 1 changes, the position of an element which receives the real image of the laser spot moves on the photoelectric converter (linear image sensor) 17 corresponding to the change in height of the inspection object 1. Therefore, the surface height information of the inspection object 1 involving the laser spot irradiated thereon is detected as position information of a receiving element on the photoelectric converter (linear image sensor) 17. By using the light beam deflector 14, a laser spot is scanned from A to B and B to A on the inspection object 1. The photoelectric converter (linear image sensor) 17 generates a signal which represents the position information of a receiving element corresponding to the height information on the inspection object 1 successively corresponding to the scanning of the laser spot by the light beam deflector 14 on the inspection object and the scanning of the XY-stage.

The height detection optical system 6 may be provided so that the laser beam reflected on the reflecting mirror 15 is irradiated on an inspection object perpendicularly, and the reflected laser beam is detected in the inclined direction through the reflecting mirror 16, or it may be provided so that the laser beam is irradiated in the inclined direction and the reflected laser beam is detected in the overhead direction or in an inclined direction on the reflecting side. In this embodiment two reflecting mirrors are used, but a structure in which the laser beam is irradiated directly and an image is detected through a reflecting mirror or a structure in which the components are arranged inversely may be employed.

As the photoelectric converter 17, one dimensional image sensors, image dissectors, or TV cameras may be used, and as the position detector of a laser spot image, position detecting elements such as Pin photodiodes may be used. As the light beam deflector 14, galvano mirrors, polygon mirrors, rotation parallel mirrors, and AO deflectors may be used.

To detect the 3D profile of an inspection object 1, first the X-stage is moved at a constant speed in the direction perpendicular to the scanning direction (A-B scanning direction shown in FIG. 2) of the laser spot by the light beam deflector 14 (for example X direction or Y direction), thereby, the inspection object 1 is scanned two-dimensionally (only X-, or Y-stage may be used). The successive scanning is carried out for each window and, after the completion of the profile detection of the first page, the Y-stage is moved by a certain distance horizontally in the scanning direction of the laser spot by the light beam deflector 14, and the X-stage is moved at a constant speed in the reverse direction to the first page to detect the profile of the second page. Following these operations, stage scanning is continued in the same manner to go to the next page. A series of these operations results in the detection of a 3D profile signal (image signal which represents a 3D profile) which covers the whole surface of the inspection object 1 as the position information of a light receiving element on the photoelectric converter (linear image sensor) 17. The position information signal of a light receiving element generated from the photoelectric converter (linear image sensor) 17 is further curve-interpolation-processed to obtain more accurate height information of the inspection object 1. In detail, a two dimensional position ordinate (two dimensional position ordinate comprising X and Y) on the inspection object 1 on which the laser spot is irradiated can be obtained by feeding inputs of the displacement in X and Y directions measured by a displacement measuring device on the XY-stage and inputs of the rotational scanning of the light beam deflector 14 in the 3D profile signal generating part 7. The height information on the inspection object 1 in the 3D profile signal generating part 7 can be obtained by feeding an input signal generated from the photoelectric converter (linear image sensor) 17. Thereby, a signal (data) which represents a 3D profile is obtained in the 3D profile signal generating part 7 from a signal which represents the height (displacement in Z-axis) of the inspection object 1, and corresponds to a two dimensional position ordinate scanned two-dimensionally (X-Y-axes direction) with the laser spot, on which inspection object the laser spot is scanned.

Next, one embodiment of an automatic focusing method will be described with reference to FIG. 3.

Figure 3A:
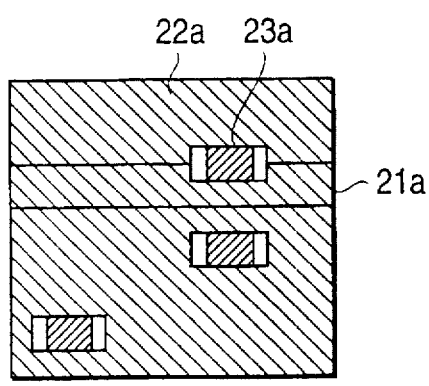
FIGS. 3(a) through 3(d) are diagrams for describing a board height detection method which may be used by the board height detection device shown in FIG. 1 in accordance with the present invention.
Figure 3B:
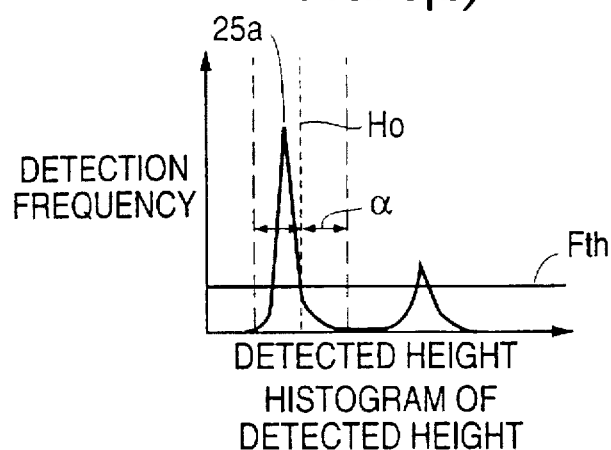

First, an example of operation of the board height detection part 9 shown in FIG. 1 will be described. The images shown in FIG. 3A and FIG. 3B represent a portion of an image included in one page obtained by stage scanning. Windows 21a and 21b are examples of regions for detecting the height of a board surface (referred also as board height hereinafter). In FIG. 3, 22a and 22b represent board regions and 23a and 23b represent part-mounted regions.

As shown in FIG. 3, the board height detection part 9 operates a histogram (frequency distribution of height) of detected height data from a signal which represents a 3D profile in the windows 21a and 21b generated in a 3D profile signal generating part 7, and this part 9 detects the minimum value among detected height peaks which appear when the detection frequency exceeds a prescribed threshold value Fth as the board height at the center position in each window. However, when the area of a board region in a window is small, a peak which exceeds the threshold value Fth can not appear in the height corresponding to the board height, thereby causing erroneous detection. To avoid such erroneous detection, the validity of the detected board height is judged using the range of deviation from the height $H_0$ of a focal plane (standard value) of the optical system.

Figure 3C:
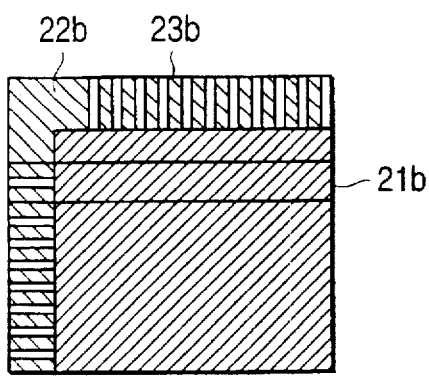
Figure 3D:
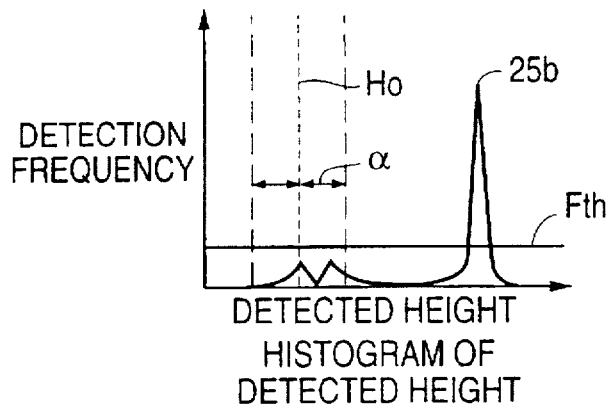

FIG. 3A shows an example of a region where the part-mounting density is low, the peak 25a is detected as the board height from the height histogram (frequency distribution of height) shown in FIG. 3B. FIG. 3C shows an example of a region where the substrate is scarcely exposed, for example by large parts such as a QFP (Quad Flat Package: a flat package with leads (terminals) 193 on the four directions) mounted on the substrate, whereby the peak 25b is detected as the board height from the height histogram (frequency distribution of height) shown in FIG. 3D. However, the height of the peak 25b is actually the surface height of the mounted parts. According to the present invention, the detected height is judged as valid when the difference between the detected board height and the height (standard value) $H_0$ of a focal plane of the optical system is within a certain range $\pm\alpha$, namely within a valid deviation range, and the board height is judged to be invalid when the detected height is not within the valid range, because the stage height is controlled so as that the board is detected consistently with reference to the height of a focal plane of the optical system as described hereinafter. Therefore, the case of FIGS. 3A and 3B is judged to be valid, and the case of FIGS. 3C and 3D is judged to be invalid.

Next, another example of the operation of the board height detection part 9 will be described with reference to FIG. 4.

Figure 4A:
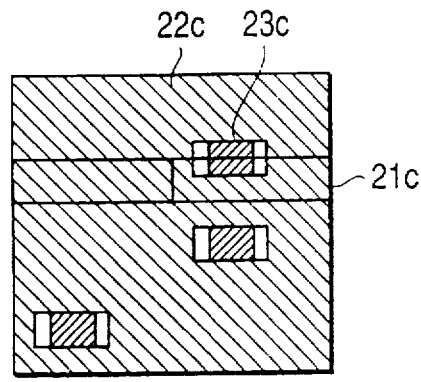
FIGS. 4(a) through 4(d) are diagrams for describing another board height detection method which may be used by the board height detection device shown in FIG. 1 in accordance with the present invention.
Figure 4B:
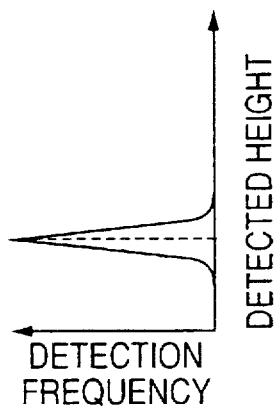
Figure 4C:
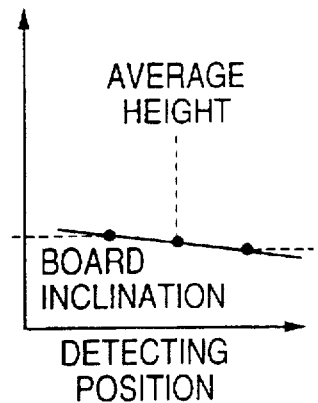
Figure 4D:
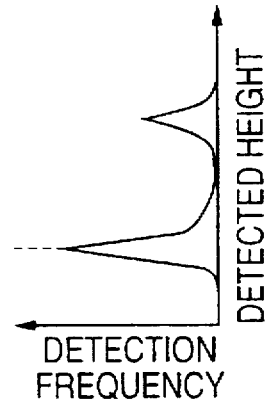

In FIG. 4A, 21c represents a window, 22c a board region, and 23c a part-mounted region. First, the window 21c is divided into two equal parts in the width direction as shown in the figure, and histograms (frequency distribution of height) of detected height data for each of the right and left bisected regions are obtained. The board height at the center position of each region is detected by the method described with reference to FIGS. 3(a) and 3(b) and the validity is judged. When valid board heights are detected for both regions, the average height (shown in FIG. 4C) of the board height obtained from the histogram of the left-side half region shown in FIG. 4B and the board height obtained from the histogram of the right-side half region shown in FIG. 4D is assigned as the board height at the center position of the window 21c, the gradient of a line connecting the detected board heights is calculated as shown in the figure, and then the gradient is assigned as the board inclination in the width direction of the window. On the other hand, when a valid board height is detected for only one region, the valid detected board height is assigned as the board height at the center position of the window, and the board inclination in the width direction of the window is assigned as zero. When no valid board height is detected for both regions, the detected board height is designated as invalid.

As described above, by dividing a window, followed by detection of the board height for each region, the detection accuracy is improved. A window may be divided into many parts and the board height of each region may be detected at the center position, and then the board height at the center position of the window and the board inclination in the width direction of the window can be determined from a least square approximated straight line of points where valid board heights are detected.

Next, an example of the operation of the board height forecasting part 10 shown in FIG. 1 will be described.

First, when an image is detected for the position corresponding to a window center, the height of a Z-stage is read in from a Z-stage control part 4. Then, when the detection of the image in the window is completed, the board height in the window is detected according to the above-mentioned method using a histogram by the board height detection part 9. The board height or inclination in the next window which is to be scanned subsequently to the above-mentioned window is forecasted by a method described herein under, the method applied to the forecasting being different depending on the validity of the detected board height. The control speed of the Z-stage in the Z-stage control part 4 is set based on the forecasting by a feedforward method.

The method for forecasting a board height or inclination in a window to be scanned next will be described for the cases in which a detected board height is valid and invalid, respectively.

Figure 5A:
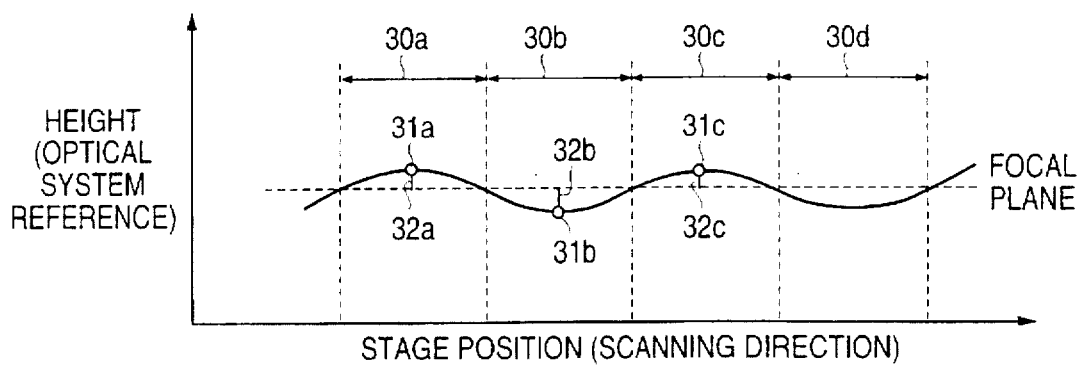
FIGS. 5(a) and 5(b) are a set of graphs for describing a board inclination forecasting method using linear approximation when the detected board height is valid in accordance with the present invention.
Figure 5B:
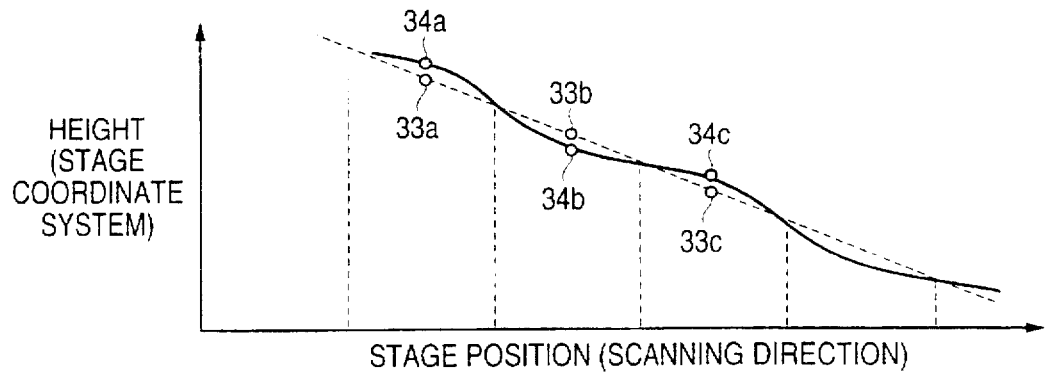

First, for the case in which the detected board height is valid, the method for forecasting a board inclination will be described with reference to FIG. 5. The axes of abscissa of FIGS. 5A and 5B represent the positions in the direction of scanning of the stage; on the other hand, the axis of ordinate of FIG. 5A represents the detecting optical system-based board surface height and the axis of ordinate of FIG. 5B represents the height of a board surface from the focal plane of the optical system and the stage-based board surface height. The stage-based coordinate system is fixed to the stage, and the origin of the coordinate moves as the stage moves in the Z direction, and if the stage height changes by $\Delta z$, the focal plane height of the stage-based optical system changes by $-\Delta z$.

In FIG. 5A, 30a to 30d represent respective windows. Now the situation at the time when scanning of the window 30c is completed will addressed. Optical system-based board heights 31a to 31c have been already detected and memorized (recorded), and the differences 32a to 32c between the board height and the focal plane height of the optical system have been calculated. On the other hand, in FIG. 5B, the stage height was read at the center position of each window, thereby, focal plane heights 33a to 33c of the stage-based optical system already have been detected and memorized (recorded). Stage-based board heights 34a to 34c are calculated from the focal plane heights 33a to 33c of the optical system and the differences 32a to 32c between the board height and the focal plane height. In this case, the board heights 34a to 34c in windows 30a to 30c represent the real profiles of the board. It is well known from experience that the profile of a board will not change rapidly because of high rigidity of the board, and so the least square approximated straight line can be obtained from the board heights 34a to 34c, and the board inclination of the next window 30d is estimated to obtain the inclination.

The method described above represents an example in which a least square approximated straight line is obtained using three point data, however, the inclination of a straight line connecting two points of the board heights 34b and 34c in the windows 30b and 30c may be assigned as the board inclination in the next window 30d, or the least square approximated straight line may be obtained from board heights of more than three points, including windows preceding the window 30a.

One example of the control speed setting of the Z-stage based on the forecasted board inclination will be described with reference to FIG. 6.

Figure 6:
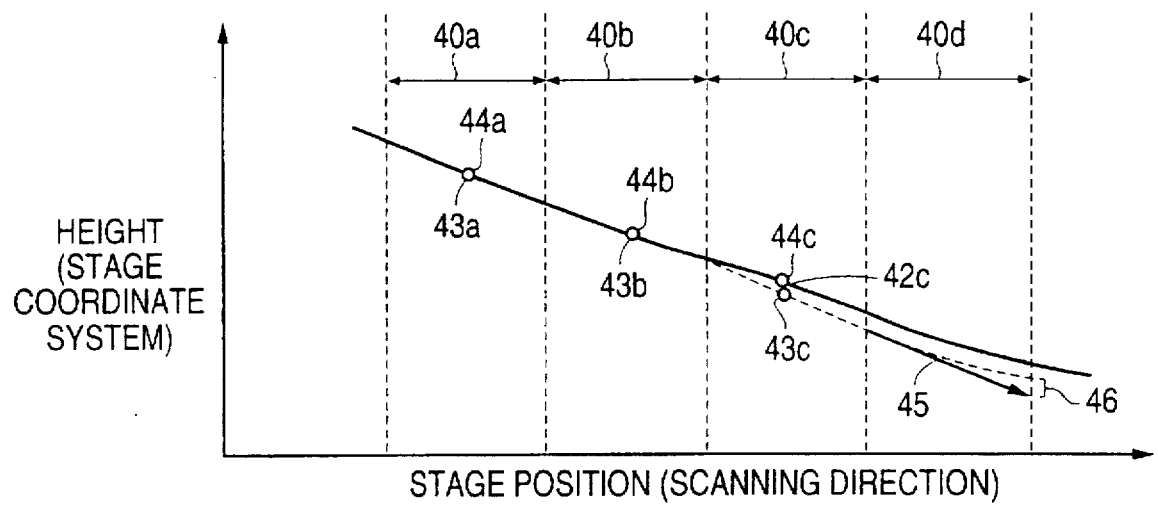
FIG. 6 is a graph for describing a method for controlling a Z-stage in accordance with the present invention.

The abscissa in FIG. 6 represents the position in scanning direction of the stage, and the ordinate represents the stage-based focal plane of the optical system for the rough dotted line and represents the stage-based board surface height for the solid line as in FIG. 5B. In the figure, at the time when scanning of a window 40c has been completed, stage-based focal plane heights 43a to 43c of the optical system have been detected, and also a difference 42c between the focal plane height of the optical system and the board surface height in the window 40c has been calculated. Stage-based board heights 44a to 44c are calculated, in the same manner as for FIG. 5B, from the focal plane heights 43a to 43c of the optical system and the difference 42c. The inclination of the least square approximated straight line of the board heights 44a to 44c in windows 40a to 40c is obtained, and a inclination 45 is assigned as the forecasted board inclination in a window 40d. The control speed of the Z-stage is set at the height where the focal plane of the optical system reaches the end of the window 40d when the stage is moved along the board inclination 45, and the speed to reach the total height of the height at the end and a correction height value 46, and position information are set. The correction 46 is a value which is obtained by multiplying a fraction of zero or more and one or less predetermined for the difference by the difference 42c. As described above, the control speed of the Z-stage or position information is set, thereby, the focal plane of the optical system is controlled so as to move parallel to the board inclination 45, and when the focal plane of the optical system deviates from the board height due to changing of the board inclination, the correction 46 acts to minimize the deviation.

Otherwise, the board height, instead of the board inclination 45, is obtained from the least square approximated straight line, and the control speed of the Z-stage or the height position may be set so that the height of the focal plane of the optical system coincides with the board surface height at the end point of the window 40d.

Next, the method for forecasting board inclination when the detected board height is invalid will be described with reference to FIG. 7.

Figure 7:
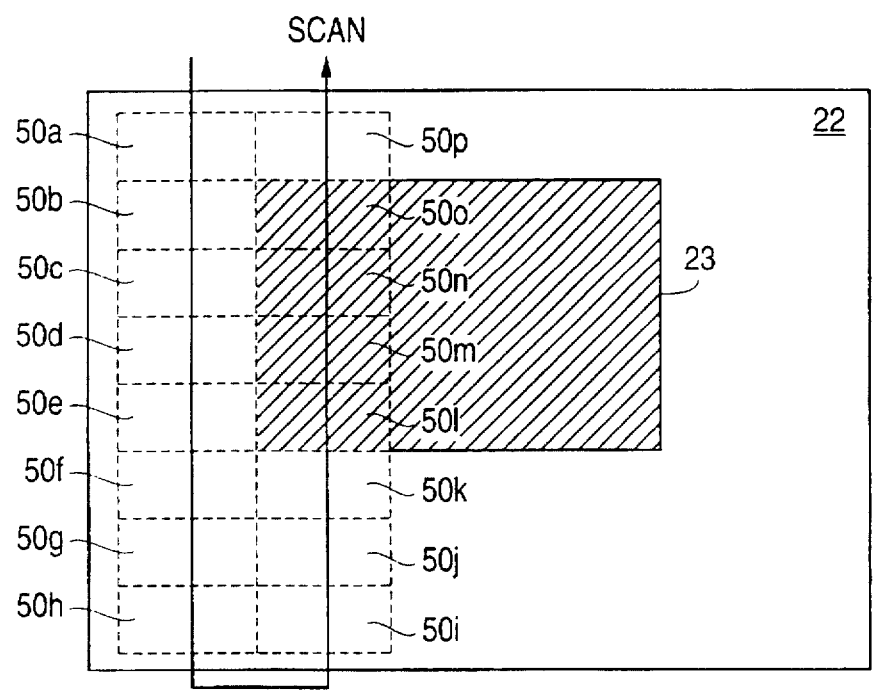
FIG. 7 is a diagram for describing a board inclination forecasting method using planar approximation when the detected board height is invalid in accordance with the present invention.

In FIG. 7, 22 represents a board region, 23 represents a part-mounted region, and 50a to 50p represent windows to be scanned. As obvious from the figure, the board height detected in windows 50a to 50k of the board region 22 among all windows 50a to 50p is valid as described with reference to FIG. 5. When the board height is judged to be valid like this, the stage-based board height is obtained from the optical system-based board height detected by the scanning and the stage height at the center of each window, an approximated straight line is obtained from the stage-based board height, and the inclination of the straight line is assigned as the board inclination in the next window.

However, when the scanning proceeds to the part-mounted region 23, the board height detected in the window 50l in the part-mounted region 23 is judged to be invalid, therefore, the board inclination in the window 50m can not be forecasted by the method described with reference to FIG. 5 and FIG. 6. Then, a plane, which passes through the board surface heights of the newest window 50k among the windows in which a valid board height is detected, the window 50f in the preceding page adjacent to the window 50k, and the window 50d in the preceding page adjacent to the window 50m, is obtained by calculation. The control speed or height position of the Z-stage in the window 50m is set at the speed or the height at the time when the focal plane of the optical system reaches the point on the plane passing through the above-mentioned three points at the end point of the window 50m.

In contrast to the method described above, the inclination of an approximated straight line calculated from several stage-based board heights in windows in the preceding page may be assigned as the board inclination in the window 50m, and the control speed or height position of the Z-stage is set so that the focal plane of the optical system moves along the board inclination. For selection of windows, a suitable number of points may be selected around the window 50d adjacent to the window 50m in the preceding page.

Otherwise, the board inclination in the width direction of a window may be obtained by the board height detection part 9; then the board height in the window 50m is forecasted from the board height in the window 50d adjacent to the window 50m and the board inclination in the width direction of the window obtained already; and the control speed or height position of the Z-stage is set so as that the focal plane of the optical system reaches the forecasted board height at the center position of the window.

As described hereinbefore, the method for obtaining the board surface height from a plane passing through three points of the board height already detected and another method for obtaining the board inclination from an approximated straight line of several board heights in the preceding page are applicable for a part-mounted region 23 to make the board surface coincide with the focal plane of the optical system; therefore, when the scanning enters again to the board region 22 at the window 50p, the detection is still possible while keeping the focus on the board surface.

After the detection of a valid board height at the window 50p in the board region 22, the board heights in windows 50l to 50o are obtained by interpolation on an assumption that the board height is on the straight line passing through the board heights at the windows 50k and 50p, which are adjacent to the windows 50l and 50o, and it is used for forecasting subsequent board inclinations.

Figure 8:
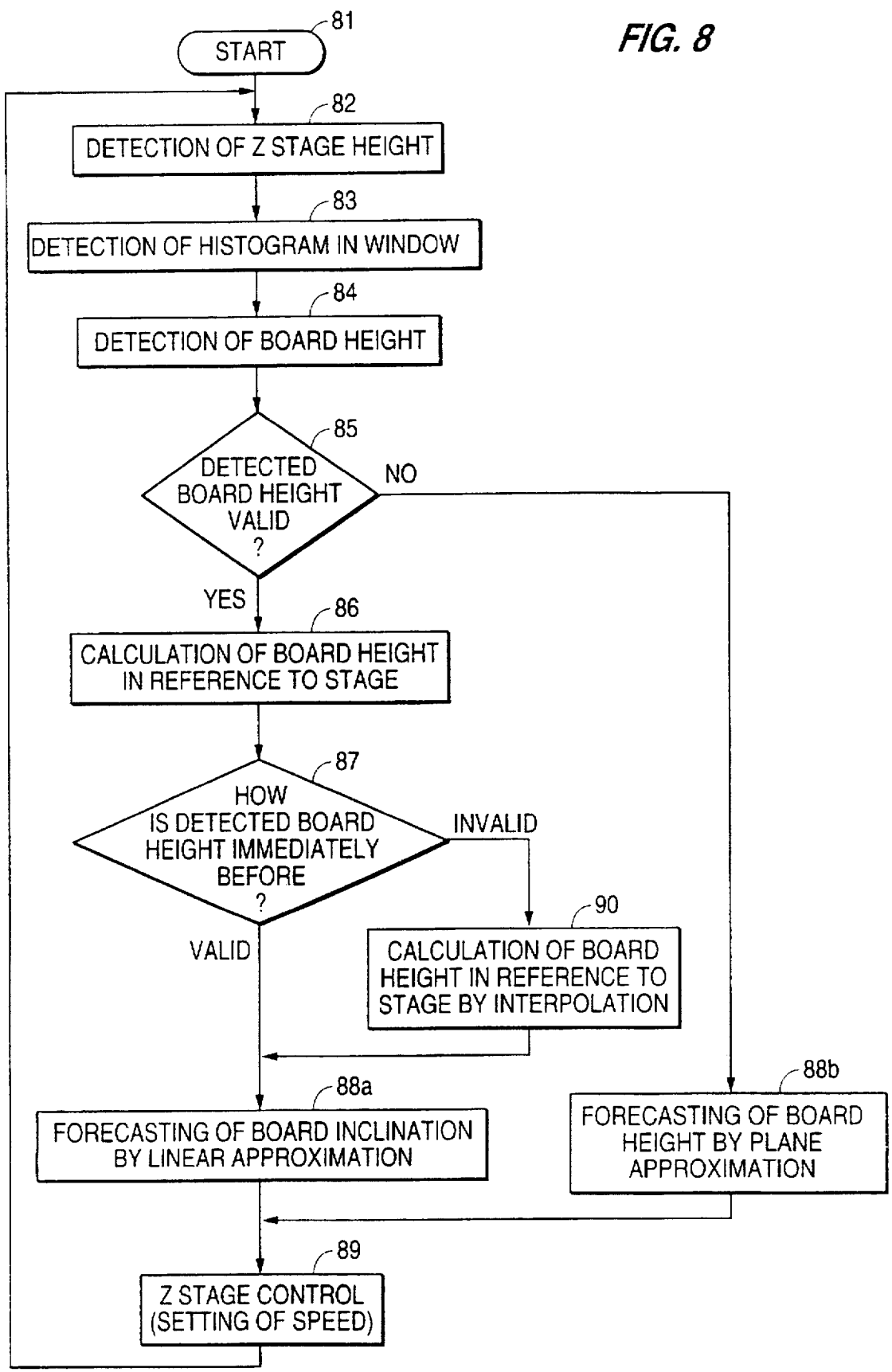
FIG. 8 is a flow chart for describing a method for automatic focusing in accordance with the present invention.

In FIG. 8, a flow chart of an automatic focusing in accordance with the present invention, which summarizes the description provided hereinbefore, is shown.

First from starting up at 81, the height of the Z-stage is detected at 82 where the board height including mounted parts is detected from a 3D profile signal obtained from the 3D profile signal generating part 7, a histogram (frequency distribution of height) in each window is detected successively at 83, and the board height having the minimum peak value in each window is detected at 84. Then, when a valid board height is detected at 85 in the board height detection part 9, a stage-based board height is calculated at 86. If the board height in the immediately preceding window is judged to be valid at 87 in the board height detection part 9, the board height forecasting part 10 forecasts at 88 the board inclination in the next window according to the linear approximation using several board height data in the newest window out of windows already scanned, and sets the control speed or height position of the Z-stage based on the forecasting at 89. On the other hand, if the board height in the immediately preceding window is judged to be invalid at 87 in the board height detection part 9, the board height in windows where no valid board height is detected is calculated at 90 according to interpolation. Then, the board height forecasting part 10 forecasts at 88a the board inclination in the next window according to the linear approximation using several board height data in the newest scanned window, and the control speed or height position of the Z-stage is set at 89 based on the forecast according to a feedforward method.

On the other hand, when a valid board height can not be detected from the histogram in the window at 85 in the board height detection part 9, the board height forecasting part 10 forecasts the board inclination and height in the next window according a planar approximation using the three already-detected board height data at 88, and based on the forecast, the control speed or height position of the Z-stage is set according to a feedforward method at 89.

Figure 9:
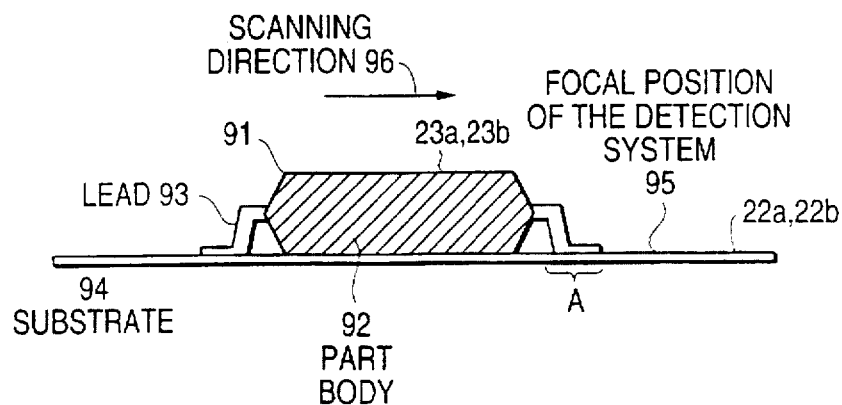
FIG. 9 is a schematic diagram for illustrating the detection of an image signal which shows a 3D profile detected from a part-mounted board with reference to the surface of the board itself in accordance with the present invention.

By repeating the above-mentioned processing, as shown in FIG. 9, surface heights 22a and 22b of a substrate 94 are made to coincide consistently with a focal plane 95 of the optical system regardless of whether a part 91, comprising a part body 92 and leads 93, is mounted on the substrate 94 or not. The arrow 96 in FIG. 9 represents the scanning direction.

In the embodiment of the present invention as described above, board heights are detected for a certain section using the detected 3D profile signal, the board height or inclination in the next section is forecasted based on board heights of a plurality of sections, and the stage height is controlled based on the forecast according to a feedforward method; therefore, the board heights 22a and 22b on the substrate 94 are made to coincide consistently with the focal plane 95 of the optical system, as shown in FIG. 9, regardless whether a part 91 is mounted or not, and thus a joint A of solder around the surface of the substrate 94 can be detected accurately and consistently.

According to the present invention, the validity of a detected board height is judged, and if the detected height is invalid, the board height or inclination in the next section is forecasted using valid board height data relating to other sections; therefore, on a place where a part 91 is mounted, the board height is made to coincide with the focal plane of the detecting optical system, as shown in FIG. 9. Therefore, also at the boundary of a part 91, where a joint A such as solder is laid, the focus does not deviate, and thus continuous and high speed scanning is possible. The effect described herein allows the apparatus of the present invention provides 3D profile detection which can accurately detect at a high speed the board height of a significantly warped part-mounted board based on the corrected or controlled 3D profile signal.

Figure 10:
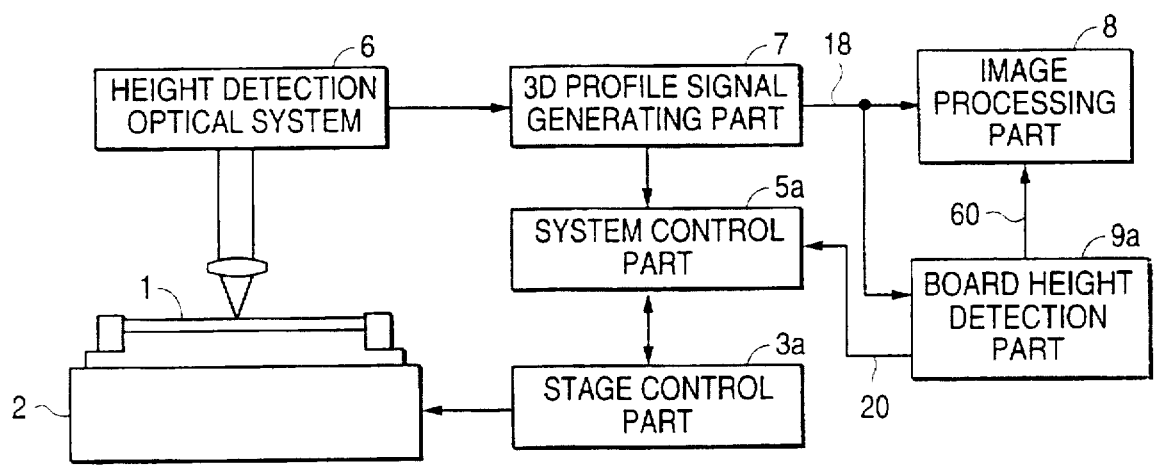
FIG. 10 is a block diagram for illustrating the integrated structure of another embodiment of an image processing device for processing an image signal of a 3D profile of a part-mounted board in accordance with the present invention.

An embodiment in accordance with the present invention similar to the embodiment shown in FIG. 1 is shown in FIG. 10. FIG. 10 is a structural diagram for illustrating the embodiment of a 3D profile detection apparatus according to the present invention. A part-mounted board (simply referred to as a board hereinafter) 1 to be inspected is supported on a stage 2 and controlled by a stage control part 3a in X, Y, and Z directions. A system control part 5a is provided for controlling the operation of the whole apparatus. The height detection apparatus comprises a height detection optical system 6 and a 3D profile signal generating part 7. An image processing part 8 is provided for detecting the state of mounting of parts and the state of a joint, such as a solder joint, on a board 1 by comparing a 3D profile image signal with the normal mounting state or jointing state based on a detected 3D profile image signal with correction or control. A board height detection part 9a is provided for detecting a board height based on a detected 3D profile image signal.

Figure 11:
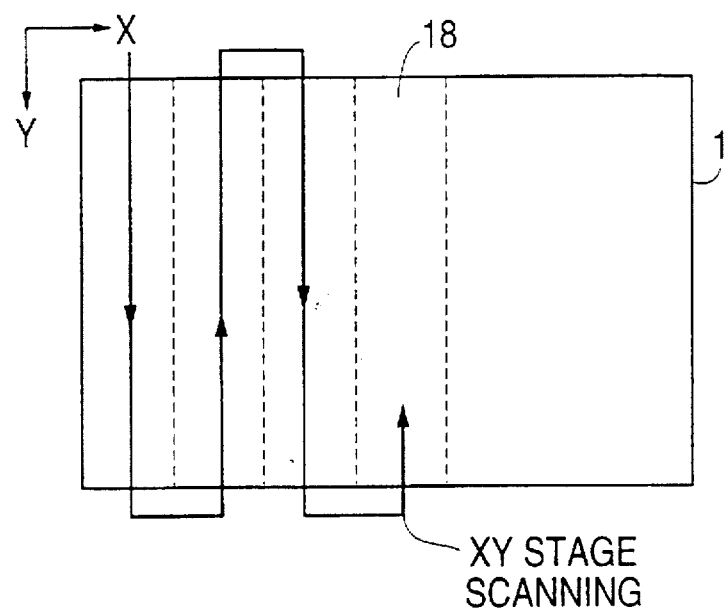
FIG. 11 is a diagram for describing a method of scanning for detecting the whole area of a part-mounted board to be inspected in accordance with the present invention.
Figure 12:
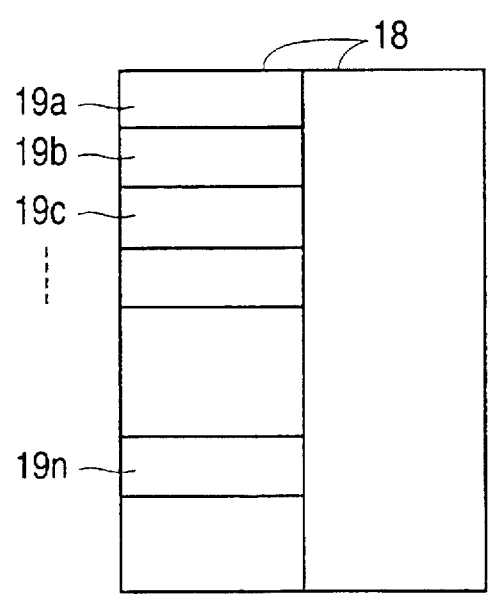
FIG. 12 is a diagram for describing a regional image generated from the 3D profile generating part shown in FIG. 1 and FIG. 10.

To detect a 3D profile image which covers the whole surface of a board supported on the stage 2, in the height detection optical system 6, for example, periodic self scanning is carried out in the X direction (in the direction parallel to the paper plane and the board 1) using a light beam deflector 14, and simultaneously the stage 2 is scanned in the Y direction (in the direction perpendicular to the paper plane). The width of scanning in the X direction of the height detecting optical system 6 is usually narrow in comparison with the width of the board 1; therefore, to scan the whole area of the board, the image is detected with continuous stage scanning in the Y direction and intermittent stage scanning in the X direction, as shown in FIG. 11. The shape of a 3D profile image signal 18 generated from the 3D profile generating part 7 is rectangular, as shown in FIG. 12; the detected image signal 18 is fed successively to the board height detection part 9a and the detected image signal 18 is divided into regions 19a to 19n with a certain size; and the board surface height is continuously detected for each region. In the system control part 5a, the degree of control for the Z-stage is operated based on a continuously-detected board surface height 20, and the Z-stage is controlled continuously through the stage control part 3a so that the distance between the height detection optical system 6 and the board 1 is kept constant. Thereby, the 3D profile image signal 18 is detected from the height detection optical system so as that the board plane is kept in a plane consistently without the affect of any warp, if the board 1 is warped.

Figure 2:
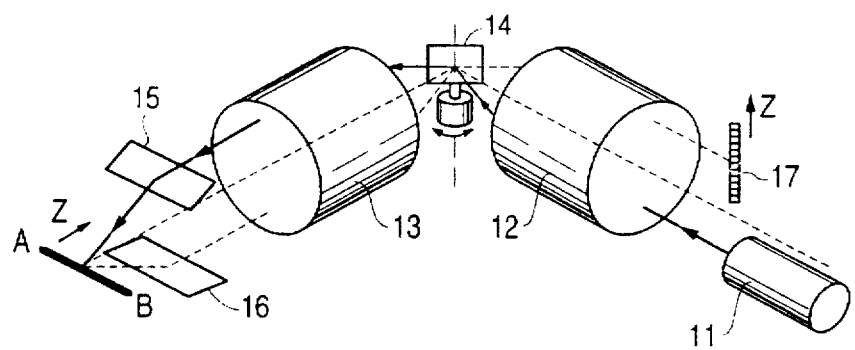
FIG. 2 is a structural diagram for illustrating one embodiment of a height detection optical system used in FIG. 1.

One structural example of the height detection optical system 6 is shown in FIG. 2. Both optical axes of a Fourier transformation lens 12 and another Fourier transformation lens 13 are laid on the same plane perpendicular to the axis of rotation of the light beam deflector 14, and are provided so as to cross each other on the light beam deflector 14. A laser beam source 11 and a photoelectric converter 17 are provided on the object plane of the Fourier transformation lens 12. The axis of rotation of the light beam deflector 14 is provided on the Fourier transformation plane of the two Fourier transformation lenses 12 and 13. The laser beam irradiated from the laser beam source 11 is transformed by the Fourier transformation lens 12, and becomes a light flux crossing with the optical axis of the Fourier transformation lens 12 with an angle at the light beam deflector 14. The light flux reflected on the light beam deflector 14 is reverse-Fourier-transformed by the Fourier transformation lens 13, and projects a laser spot on an inspection object (board) 1 through a reflecting mirror 15. The laser spot is scanned in A-B direction on the inspection object 1 by rotating the light beam deflector 14. The laser spot enters into the Fourier transformation lens 13 through a reflecting mirror 16, and forms a Fourier-transformed image on the light beam deflector 14. The Fourier-transformed image is reflected by the light beam deflector 14, is reverse-Fourier-transformed by the Fourier transformation lens 12, and forms a real image of the laser spot on the photoelectric converter 17. When the height of the inspection object 1 changes in the Z direction, the real image of the laser spot moves on the photoelectric converter 17 in the Z direction. In the 3D profile signal generating part 7, the height of the inspection object 1 is operated based on a signal corresponding to the displacement on the photoelectric converter 17 obtained from the photoelectric converter 17, and the height is assigned as a 3D profile signal. A two dimensional position coordinate is obtained by a scanning of the laser spot by the light beam deflector 14 and by displacement (scanning) in the X and Y directions of the inspection object 1 by the XY-stage.

The optical system 6 may be provided so that the laser beam reflected on the reflecting mirror 15 is irradiated on the inspection object 1 perpendicularly and the reflected laser beam is detected in the inclined direction through the reflecting mirror 16. Otherwise, the optical system 6 may be provided so that the laser beam is irradiated in the inclined direction and the reflected laser beam is detected in the overhead direction. In this embodiment, two reflecting mirrors are used, but an structure in which the laser beam is irradiated directly and an image is detected through a reflecting mirror, or a structure in which the components are arranged inversely, may be employed. As the photoelectric converter 17, one dimensional image sensors, image dissectors, and TV cameras may be used. Otherwise, as the position detector of a laser spot, position detection elements, such as Pin photodiodes, may be used. As the light beam deflector 14, galvano mirrors, polygon mirrors, rotation parallel mirrors, and AO deflectors may be used. As the height detection optical system 6, any system which can detect a 3D profile of an object by optical means, such as a system in which a light beam is irradiated through a slit and a light cut line is detected by a TV camera may be used in place of the elements in the above-mentioned systems.

Next, the operation of the board height detection part 9a will be described with reference to FIG. 3. Images shown in FIGS. 3A, 3B, 3C, and 3D show a portion of a 3D profile image obtained by self-scanning by the height detection optical system 6 and scanning of a Y-stage and histograms (frequency distribution of height) in partial regions 21a and 21b in the image, respectively. The regions 21a and 21b in the images are one example of a region with a certain size for detecting a board height. A region 22 is a region where the board surface is detected and a region 23 is a region where parts are mounted. FIGS. 3A and 3B show a case in which the part-mounting density is low and the board area is large in the region 21a. On the contrary, FIGS. 3C and 3D show a case in which the board area is small in the region 21b because large parts, such as QFP (Quad Flat Package: four direction flat package), are mounted therein. Similar situation occurs when the part-mounting density is high.

First, as shown in FIGS. 3B and 3D, histograms of height data in the region 21 are produced. When the board is not warped, parts are not mounted, or the density of part-mounting is low, the peak height of a histogram corresponds to the board height. Therefore, in such a case, the height of the maximum peak in a histogram is detected and the height is used as the board height. By this method, the board height is obtained very easily. However, when the part-mounting density is high or the board is warped, the shape of a histogram is not an ideal shape which has only one peak. In this case, the minimum value among detected heights having peaks of the frequency exceeding a threshold value Fth, which is determined from the area (number of picture elements) in the region for operation of the histogram, is assigned as the board height in the region 21. Thereby, the misdetection of the height of the upper surface of parts for the board surface height is mitigated. If there is no peak exceeding the threshold value Fth, the height detection of the board surface is judged to be invalid in the region.

The peak 25a in FIG. 3B and the peak 25b in FIG. 3D are detected as the minimum heights having a frequency exceeding the threshold value Fth. However, the peak 25b is not the board height, but the height of the upper surface of parts. In the case in which the board area occupies only a small proportion in the region 21 as shown in FIG. 3C, a peak which exceeds the threshold value Fth appears as not consistent with the detected height corresponding to the board height. To avoid misdetection of the board height in such case, the board height, which is originally set, or the ideal board height, is assigned as the standard value $H_0$, and the detected height of the highest frequency exceeding the threshold value Fth within a range of standard value $\pm\alpha$ is detected as the board height in the region 21. The value $\alpha$ can be determined previously based on the surface roughness of a board and the allowable maximum warp of a board. The standard value $H_0$ is determined based on the board height already detected in a region near the region or is the value of the focal plane of the height detection optical system 6 as the ideal distance value between the height detection optical system 6 and the surface of the board 1.

When there is no detection height which satisfies the above-mentioned condition, the board height detection in the region is judged to be invalid. Therefore, the peak 25a in FIG. 3B is judged to be valid as the board height, but the peak 25b in FIG. 3D is judged to be invalid. Thereby, the misdetection of the part upper surface for the board surface height is prevented.

When a valid board height is detected, the stage controlling is operated by the system control part 5a based on the detected board height 25a, the Z-stage is driven through the stage control part 3a, and thus it becomes possible that the distance between the height detection optical system 6 (3D profile detection optical system) and the surface of the board 1 itself is controlled to be constant.

When the detected board height is judged to be invalid, the valid detected board height which was already detected by the board height detection part 9a on regions near the addressed region is used as the board height as it is, or the board height is determined according to the extrapolation of linear or planar approximation using a plurality of valid detected board heights which were already detected in regions near the addressed region.

Thereby, even if the part-mounting density on a board 1 is high or the board 1 is warped, the board surface height is detected or determined by operation consistently without any affect of the high part-mounting density and warp, and the 3D profile can be detected as if the board surface were laid on a flat plane always.

Otherwise, instead of controlling the distance between the height detection optical system 6 (3D profile detection optical system) and the surface of a board 1 itself, the image signal can be detected while the Z-stage height is maintained fixed in the height detection optical system 6 and the 3D profile signal generating part 7. For this purpose, the board surface height is detected from the detected 3D profile image signal according to the method described hereinbefore, and the 3D profile image signal (constituted with three dimensional coordinate information) 18 is corrected by a correction signal 60 in synchronism with image detection to obtain a correct Z-coordinate axis (height information) so that the detected board surface height is maintained at a constant value, whereby the same effect is obtained. In this case, it is required that the height information of a board 1 including mounted parts (height data) is obtained accurately by the height detection optical system 6 even if the focus deviates seriously. The detection optical system in the height detection optical system 6 may be constituted with a double side telecentric optical system, whereby this purpose is accomplished.

As described above, the 3D profile image signal 18 is corrected based on the correction signal 60 to obtain a correct Z-coordinate axis (height information), thereby, the 3D profile image signal (constituted with three dimensional coordinate information) based on the surface of a board 1 itself is obtained. Thus, in an image processing part 8, the setting of the standard height position becomes easy in comparison with the normal state of mounting and jointing; as the result, the comparison processing with the normal state of mounting and jointing becomes easy, and so the state of part mounting on a board 1 and the state of jointing of a joint, such as a solder joint, can be inspected reliably.

In FIG. 13, another example of the operation of board height detection part 9a for detecting a board surface height from a 3D profile image is shown. First, the region 21 is divided into n-pieces in the same direction as the self-scanning direction of the height detection optical system 6. Then, a histogram is produced in each divided region, the board surface height of each region is detected according to the method described above, and the validity is judged. The average value is operated using only a valid board surface height detected in each divided region, thereby, the overall board height of the region 21 is obtained. Not only the overall board height, but also the inclination of the region 21 in the scanning direction of the height detection optical system 6 is obtained by using a valid board height in each region. As described herein, a board height detection region is divided, and the board height is detected in each region, thereby, the height detection accuracy is improved.

In the method in which, instead of controlling the distance between the height detection optical system (3D profile detection optical system) 6 and the surface of a board 1 itself, an image is detected, while the Z-stage height is maintained fixed, the board surface height is detected from a detected 3D profile image, and the 3D profile image signal 18 is corrected in synchronism with image detection to keep the detected board surface height at a constant value, by correcting the board height detected in each divided region and using the corrected value as the detected board height in each region. The 3D profile image signal 18 including mounted parts used in the comparison inspection with the normal state of mounting and jointing performed in the image processing part 8 is corrected to give the corrected board height accurately.

Figure 14:
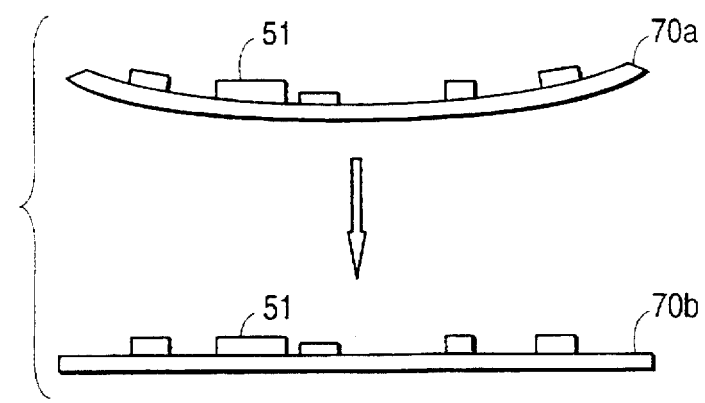
FIG. 14 is a schematic diagram for illustrating the concept of controlling or correcting an image signal of a 3D profile of a part-mounted board taking into consideration the warp of the board itself in accordance with the present invention.
Figure 15A:
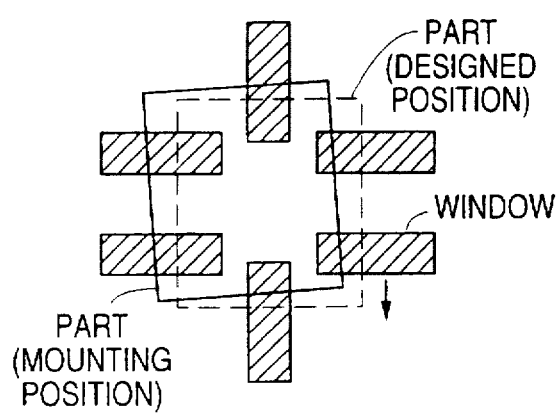
FIG. 15(a) is a schematic diagram for illustrating one example of conventional methods for height detection of a warped board with FIG. 15(b) showing a histogram.
Figure 15B:
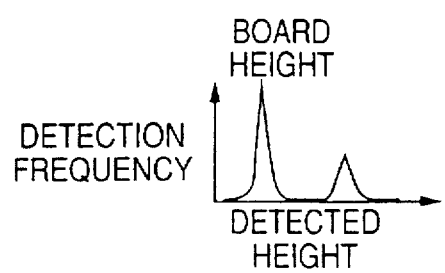
Figure 16:
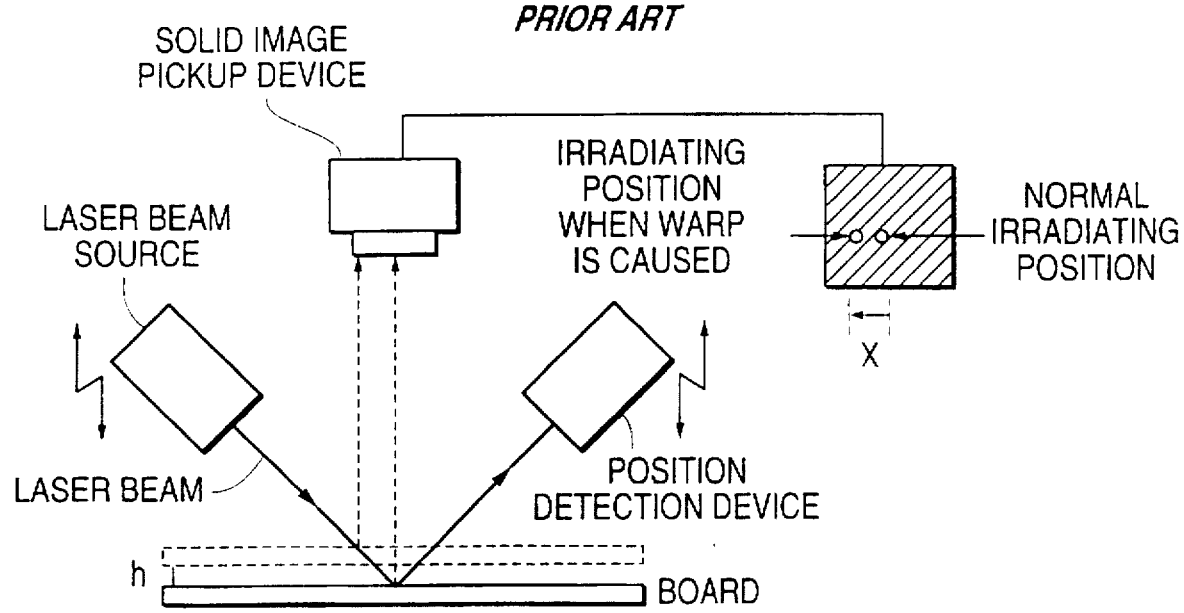
FIG. 16 is a schematic diagram for illustrating one example of conventional methods for focusing on a warped board.
Figure 17:
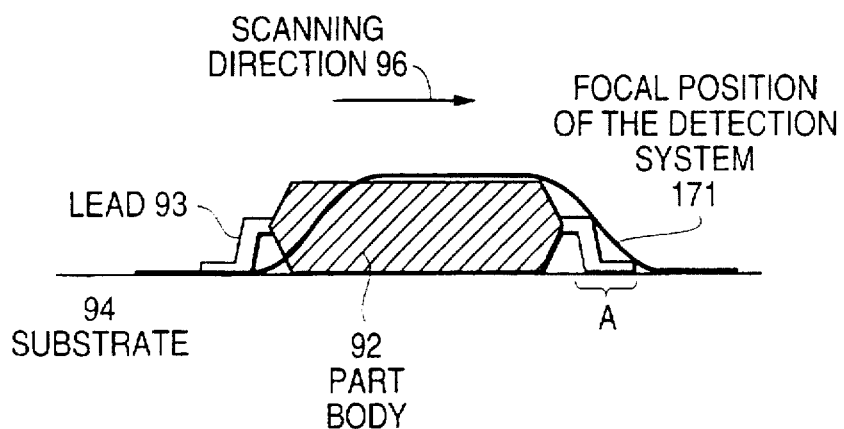
FIG. 17 is a schematic diagram for illustrating the motion of a focal position on a part-mounted board involving control delays.
Figure 18:
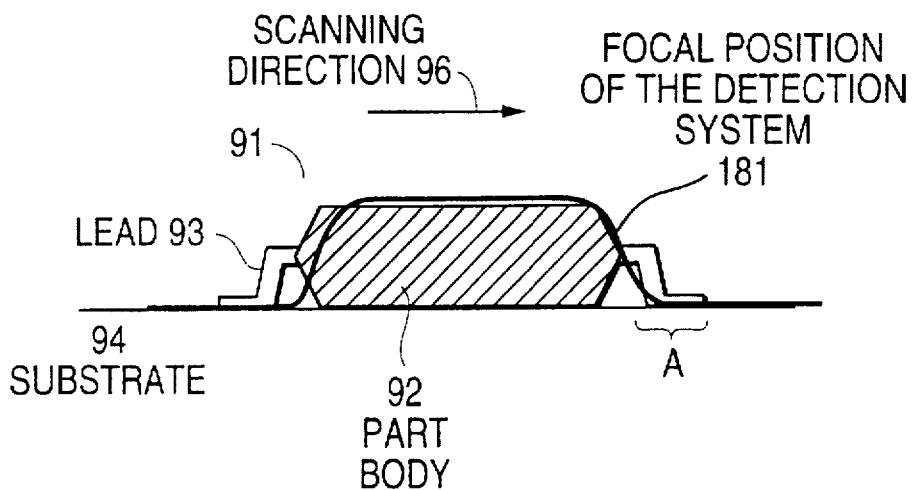
FIG. 18 is a schematic diagram for illustrating the motion of a focal position on a part-mounted board when the scanning speed is slow.
Figure 19A:
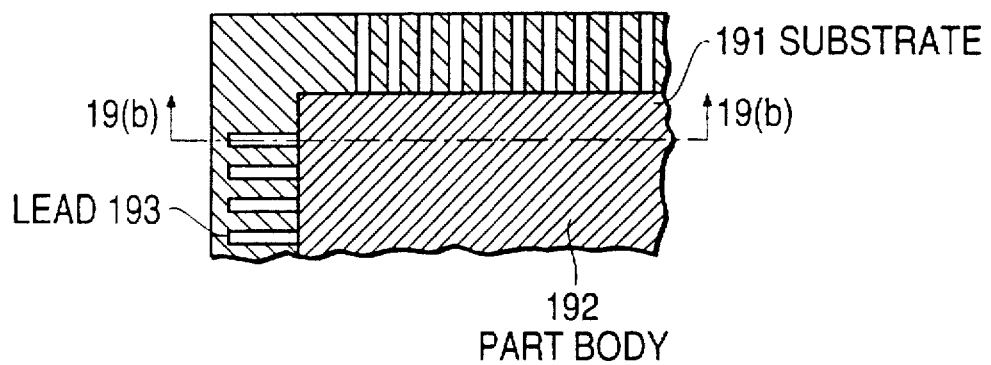
FIGS. 19(a) and 19(b) are diagrams for illustrating the case in which QFP parts are mounted on a board in accordance with the present invention.
Figure 19B:
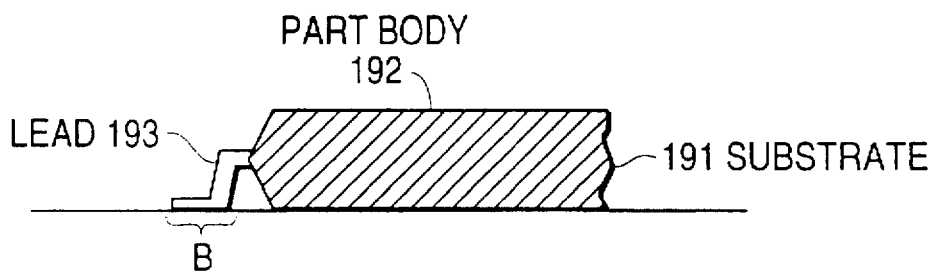

The concept of the 3D profile detection method in accordance with the present invention described hereinbefore is shown in FIG. 14. A side view of an actual substrate 70a, in this example, shows that the board center is warped in the vertical direction. A part 51 is mounted on the substrate. The board surface height of a warped board is detected as if the board surface were laid on a flat plane as shown by the board 70b in FIG. 14 without any affect by the warp by detecting a 3D profile image signal of a part-mounted board according to the 3D profile detection method in accordance with the present invention. As a result, the detected or corrected 3D profile image signal is image-processed in the image processing part 8 for comparative inspection with high accuracy, and the reliability is significantly improved.

According to the present invention, the board surface height is detected continuously and selectively regardless of whether parts are mounted on a board, and the distance between the detection optical system and the surface of the board itself is controlled continuously based on the surface height of the detected board itself; whereby, even if the board is warped, the 3D profile image signal of a part-mounted board is detected without any affects of the warp, as if the surface of the board itself were laid on a flat plane. As a result, the present invention exhibits the effect that the state of part mounting or jointing can be inspected reliably.

According to the present invention, the board surface height is detected continuously and selectively regardless whether parts are mounted on a board, and an image is corrected so as that the board surface height is maintained at a constant value in the 3D profile image based on the surface height of the detected board itself; whereby, even if the board is warped, the 3D profile image signal of a part-mounted board is detected without any affect of the warp, as if the surface of the board itself were laid on a flat plane. As a result, the present invention exhibits the effect that the state of part mounting or jointing can be inspected reliably.

According to the present invention, the above-mentioned effect is exhibited without position data of mounted parts by judging the validity of the detected board height.

According to the present invention, when applied to a part-mounted board inspection apparatus, a 3D profile image signal at joints, such as a solder joint, on the surface of a board is detected accurately by making the surface height of the board itself coincide with the focal plane of the detection optical system, and so the present invention exhibits the effect that the state of part mounting or jointing can be inspected reliably.

According to the present invention, the board surface height is forecasted regardless of whether a scanned region is a part-mounted region or not while a significantly warped part-mounted board is scanned continuously at a high speed, and the optical system is focused automatically at the forecasted board surface height consistently. Thus, the present invention exhibits the effect that the state of part mounting or jointing can be inspected reliably.

What is claimed is:

1. An automatic focusing method for a height detection optical system, in which a stage scanning region is set on a part-mounted board supported on a support stage and a three dimensional profile of the part-mounted board is detected by scanning the stage scanning region, comprising the steps of: detecting a board surface height in the stage scanning region, from a three dimensional profile signal of the part-mounted board detected by said height detection optical system; forecasting the board surface height or inclination in a portion of the stage scanning region to be scanned next from the board surface height already detected and a control history of stage height of said support stage; and controlling the speed or height of a Z-stage in a Z direction while scanning the stage scanning region so that the board surface is made to coincide with the focal plane of said height detection optical system based on said forecasted board surface height or inclination according to a feedforward method.

2. An automatic focusing apparatus for a height detection optical system, in which a stage scanning region is set on a part-mounted board supported on a support stage and a three dimensional profile of the part-mounted board is detected by scanning said stage scanning region, comprising: a control means for controlling two dimensional scanning of said support stage to scan said part-mounted board in a plurality of windows; a board height detection means for detecting and memorizing a board surface height in said plurality of windows, which are set in the stage scanning region controlled by said control means, from a three dimensional profile signal of the part-mounted board detected by said height detection optical system; a board height forecasting means for forecasting the board surface height or inclination in a next window based on said board surface height in a plurality of windows already detected and memorized by said board height detection means; and a stage height control means for controlling speed or height of a Z-stage in a Z direction according to a feedforward method so as that the board surface and a focal plane of said height detection optical system are made to coincide, based on the board surface height or inclination in the next window forecasted by said board height forecasting means.

3. A three dimensional profile detection method, comprising the steps of: using a height detection optical system to detect a three dimensional profile image signal from a part-mounted board by scanning two-dimensionally desired scanning regions of the part-mounted board; detecting a board surface height for each desired scanning region from the detected three dimensional profile image signal; controlling a distance between the height detection optical system and the part-mounted board based on the detected board surface height; and detecting a three dimensional profile image signal of the part-mounted board using the height detection optical system from a scanning region adjacent to the desired scanning region.

4. A three dimensional profile detection method, comprising the steps of: using a height detection optical system to detect a three dimensional profile image signal from a part-mounted board by scanning two-dimensionally the part-mounted board; when a frequency of the board surface height, which are within a predetermined range from a predetermined standard height, is higher than a predetermined value, detecting the board surface height for each desired scanning region from the detected three dimensional profile image signal; and, based on the detected board surface height, detecting a three dimensional profile image signal of the part-mounted board, through correction by the height detection optical system, from a scanning region adjacent to the desired scanning region.

5. A three dimensional profile detection method, comprising the steps of: using a height detection optical system to detect a three dimensional profile image signal from a part-mounted board by scanning two-dimensionally the part-mounted board; preparing from the detected three dimensional profile image signal a frequency distribution of a board surface height for each desired scanning region; in the prepared frequency distribution of the board surface height, when a detected frequency is a certain prescribed threshold value or higher and the detected value representing the board surface height lies in a range of a standard height plus or minus a prescribed error, then such detected value representing the board surface height is used for controlling a distance between the height detection optical system and the part-mounted board; and detecting a three dimensional profile image signal of the part-mounted board, using the height detection optical system, from a scanning region adjacent to the desired scanning region.

6. A three dimensional profile detection method, comprising the steps of: using a height detection optical system to detect a three dimensional profile image signal from a part-mounted board by scanning two-dimensionally the part-mounted board; preparing from the detected three dimensional profile image signal a frequency distribution of a board surface height for each desired scanning region; in the prepared frequency distribution of the board surface height, when a detected frequency is a certain prescribed threshold value or higher and a detected value representing the board surface height lies in a range of a standard height plus or minus a prescribed error, detecting the three dimensional profile image signal of the part-mounted board, through correction by the height detection optical system, from a scanning region adjacent to the desired scanning region, based on said detected value representing the board surface height.

7. A three dimensional profile detection method, comprising the steps of: using a height detection optical system to detect a three dimensional profile image signal from a part-mounted board by scanning two-dimensionally the part-mounted board; preparing from the detected three dimensional profile image signal a frequency distribution of a board surface height for each desired scanning region; in the prepared frequency distribution of the board surface height, when a detected frequency is a certain prescribed threshold value or higher and a detected value representing the board surface height lies in a range of a standard height plus or minus a prescribed error, averaging the detected value representing the board surface height for an adjacent scanning region; then, based on the detected value which represents the averaged board surface height, controlling a distance between the height detection optical system and the part-mounted board; and detecting a three dimensional profile image signal of the part-mounted board, using the height detection optical system from the adjacent scanning region.

8. A three dimensional profile detection method, comprising the steps of: using a height detection optical system to detect a three dimensional profile image signal from a part-mounted board by scanning two-dimensionally the part-mounted board; preparing from the detected three dimensional profile image signal a frequency distribution of a board surface height for each desired scanning region; in the prepared frequency distribution of the board surface height, when a detected frequency is a certain prescribed threshold value or higher and a detected value representing the board surface height lies in a range of a standard height plus or minus a prescribed error, averaging the detected value representing the board surface height for an adjacent scanning region; then, based on the detected value which represents the averaged board surface height, utilizing the detected value to correct a three dimensional profile image signal of the part-mounted board detected by the height detection optical system from the adjacent scanning region.

9. A three dimensional profile detection method, comprising the steps of: using a height detection optical system to detect a three dimensional profile image signal from a part-mounted board by scanning two-dimensionally the part-mounted board; preparing from the detected three dimensional profile image signal a frequency distribution of a board surface height for each desired scanning region; in the prepared frequency distribution of the board surface height, when a detected frequency is a certain prescribed threshold value or higher and a detected value representing the board surface height lies in a range of a standard height plus or minus a prescribed error, then based on the detected value representing the board surface height, controlling a distance between the height detection optical system and the part-mounted board; in the prepared frequency distribution of the board surface height, when the detected frequency is not the certain prescribed threshold value or higher, or the detected frequency is the certain prescribed threshold value or higher and the detected value representing the board surface height does not lie in the range of the standard height plus or minus a prescribed error, then based on a value which represents the board surface height in a neighboring scanning region, controlling the distance between the height detection optical system and the part-mounted board; and detecting a three dimensional profile image signal of the part-mounted board, using the height detection optical system, from the neighboring scanning region.

10. A three dimensional profile detection method, comprising the steps of: using a height detection optical system to detect a three dimensional profile image signal from a part-mounted board by scanning two-dimensionally the part-mounted board; preparing from the detected three dimensional profile image signal a frequency distribution of a board surface height for each desired scanning region; in the prepared frequency distribution of the board surface height, when a detected frequency is a certain prescribed threshold value or higher and a detected value representing the board surface height lies in a range of a standard height plus or minus a prescribed error, averaging the detected value representing the board surface height for an adjacent scanning region then, based on the detected value which represents the averaged board surface height, correcting the three dimensional profile image signal of the part-mounted board detected by the height detection optical system from the adjacent scanning region; in the prepared frequency distribution of the board surface height, when the detected frequency is not the certain prescribed threshold value or higher, or the detected frequency is the certain prescribed threshold value or higher and the detected value representing the board surface height does not lie in the range of the standard height plus or minus a prescribed error, then based on a value which represents the board surface height in a neighboring scanning region, detecting the three dimensional profile image signal of the part-mounted board through correction by the height detection optical system from the adjacent scanning region.

11. A three dimensional profile detection method, comprising the steps of: scanning a part-mounted board two-dimensionally to detect a three dimensional profile image using a height detection optical system; detecting a board surface height for each of a plurality of divided regions into which the detected three dimensional profile image is divided to provide regions of a prescribed size; judging a validity of the detected board surface height of the board surface; then, based on a board surface height which is judged to be valid, controlling a distance between the height detection optical system and the board surface; and detecting a three dimensional profile image signal.

12. A three dimensional profile detection apparatus comprising: a height detection optical system for scanning two-dimensionally a part-mounted board to detect a three dimensional profile image signal from the part-mounted board; and a board height detecting and controlling means for detecting a board surface height for each of a plurality of desired scanning regions from the three dimensional profile image signal detected by said height detection optical system, and for controlling a distance between the height detection optical system and the part-mounted board to detect, using the height detection optical system, a three dimensional profile image signal of the part-mounted board from a scanning region adjacent to a desired scanning region based on a detected board surface height.

13. A three dimensional profile detection apparatus comprising: a height detection optical system for scanning two-dimensionally a part-mounted board to detect a three dimensional profile image signal from the part-mounted board; and a board height detecting and correcting means for detecting a board surface height for each of a plurality of desired scanning regions from the three dimensional profile image signal detected by said height detection optical system, and for detecting the three dimensional profile image signal of the part-mounted board detected by the height detection optical system from a scanning region adjacent to a desired scanning region through correction based on the detected board surface height.

14. A three dimensional profile detection apparatus comprising: a height detection optical system for scanning two-dimensionally a part-mounted board to detect a three dimensional profile image signal from the part-mounted board; and a board height detecting and controlling means for preparing a frequency distribution of a board surface height for each of a plurality of desired scanning regions from the three dimensional profile image signal detected by said height detection optical system, and, in the prepared frequency distribution of the board surface height, when a detected frequency is a certain prescribed threshold value or higher and a detected value representing the board surface height lies in a range of a standard height plus or minus a prescribed error, for controlling a distance between the height detection optical system and part-mounted board based on the detected value representing the board surface height, whereby a three dimensional profile image signal of the part-mounted board is detected by the height detection optical system from a scanning region adjacent to a desired scanning region.

15. A three dimensional profile detection apparatus comprising: a height detection optical system for scanning two-dimensionally a part-mounted board to detect a three dimensional profile image signal from the part-mounted board; and a board height detecting and correcting means for preparing a frequency distribution of a board surface height for each of a plurality of desired scanning regions from the three dimensional profile image signal detected by said height detection optical system, and, in the prepared frequency distribution of the board surface height, when a detected frequency is a certain prescribed threshold value or higher and a detected value representing the board surface height lies in a range of a standard height plus or minus a prescribed error, for detecting the three dimensional profile image signal of the part-mounted board detected by the height detection optical system from a scanning region adjacent to a desired scanning region through correction based on the detected value representing the board surface height.

16. A three dimensional profile detection apparatus comprising: a height detection optical system for scanning two-dimensionally a part-mounted board to detect a three dimensional profile image signal from the part-mounted board; and a board height detecting and controlling means for preparing a frequency distribution of a board surface height for each of a plurality of desired scanning regions from the three dimensional profile image signal detected by said height detection optical system, and, in the prepared frequency distribution of the board surface height, when a detected frequency is a certain prescribed threshold value or higher and a detected value representing the board surface height lies in a range of a standard height plus or minus a prescribed error, for averaging the detected value representing the board surface height for an adjacent scanning region, for controlling a distance between the height detection optical system and the part-mounted board based on the value which represents the averaged board surface height, and for detecting the three dimensional profile image signal of the part-mounted board by said height detection optical system from the adjacent scanning region.

17. A three dimensional profile detection apparatus comprising: a height detection optical system for scanning two-dimensionally a part-mounted board to detect a three dimensional profile image signal from the part-mounted board; and a board height detecting and correcting means for preparing a frequency distribution of a board surface height for each of a plurality of desired scanning regions from the three dimensional profile image signal detected by said height detection optical system, and, in the prepared frequency distribution of the board surface height, when a detected frequency is a certain prescribed threshold value or higher and a detected value representing the board surface height lies in a range of a standard height plus or minus a prescribed error, for averaging the detected value representing the board surface height for an adjacent scanning region, and for detecting the three dimensional profile image signal of the part-mounted board detected by said height detection optical system from the adjacent scanning region adjacent to a desired scanning region through correction based on a value which represents an averaged board surface height.

18. A three dimensional profile detection apparatus comprising: a height detection optical system for scanning two-dimensionally a part-mounted board to detect a three dimensional profile image signal from the part-mounted board; and a board height detecting and controlling means for preparing a frequency distribution of a board surface height for each of a plurality of desired scanning regions from the three dimensional profile signal detected by said height detection optical system, and, in the prepared frequency distribution of the board surface height, when a detected frequency is a certain prescribed threshold value or higher and a detected value representing the board surface height lies in a range of a standard height plus or minus a prescribed error, then based on the detected value representing the board surface height, for controlling a distance between the height detection optical system and the part-mounted board, and, in the prepared frequency distribution of the board surface height, when the detected frequency is not the certain prescribed threshold value or higher, or the detected frequency is the certain prescribed threshold value or higher and the detected value representing the board surface height does not lie in the range of the standard height plus or minus a prescribed error, for controlling the distance between the height detection optical system and the part-mounted board based on the detected value which represents an already-detected board surface height in a neighboring scanning region, whereby the three dimensional profile image signal of the part-mounted board is detected by said height detection optical system from the neighboring scanning region.

19. A three dimensional profile detection apparatus comprising: a height detection optical system for scanning two-dimensionally a part-mounted board to detect a three dimensional profile image signal from the part-mounted board; and a board height detecting and correcting means for preparing a frequency distribution of a board surface height for each of a plurality of desired scanning regions from the three dimensional profile signal detected by said height detection optical system, and, in the prepared frequency distribution of the board surface height, when a detected frequency is a certain prescribed threshold value or higher and a detected value representing the board surface height lies in a range of a standard height plus or minus a prescribed error, for averaging the detected value representing the board surface height for an adjacent scanning region, for correcting the three dimensional profile image signal of the part-mounted board detected by the height detection optical system from the adjacent scanning region based on a value which represents the averaged board surface height, and, in the prepared frequency distribution of the board surface height, when the detected frequency is not the certain prescribed threshold value or higher, or the detected frequency is the certain prescribed threshold value or higher and the detected value representing the board surface height does not lie in the range of the standard height plus or minus a prescribed error, for detecting the three dimensional profile image signal of the part-mounted board detected by the height detection optical system from the adjacent scanning region through correction based on a value which represents an already-detected valid board surface height in a neighboring scanning region.

20. A three dimensional profile detection apparatus comprising: a height detection optical system for detecting a three dimensional profile image by scanning two-dimensionally a part-mounted board; and a board height detecting and controlling means for detecting the board surface height for each of a plurality of divided regions in the three dimensional profile image detected by said height detection optical system and divided into regions of a certain prescribed size, for judging the validity of the detected board surface height, and for controlling the distance between the height detection optical system and the board surface based on a board surface height judged to be valid so as to enable proper detection of the three dimensional profile image signal.

21. An inspection method for a part-mounted board, comprising the steps of: using a height detection optical system to detect a three dimensional profile image signal from a part-mounted board by scanning two-dimensionally the part-mounted board; preparing from the detected three dimensional profile image signal a frequency distribution of a board surface height for each of a plurality of desired scanning regions; in the prepared frequency distribution of the board surface height, when a detected frequency is a certain prescribed threshold value or higher and a detected value representing the board surface height lies in a range of a standard height plus or minus a prescribed error, then based on the detected value representing the board surface height, controlling a distance between the height detection optical system and the part-mounted board and, based on the three dimensional profile image signal obtained from the part mounted board, using the height detection optical system, from a scanning region adjacent to the desired scanning region, inspecting a state of mounting of parts or jointing on the part-mounted board.

22. An inspection method for a part-mounted board, comprising the steps of: using a height detection optical system to detect a three dimensional profile image signal from a part-mounted board by scanning two-dimensionally the part-mounted board; preparing from the detected three dimensional profile image signal a frequency distribution of a board surface height for each of a plurality of desired scanning regions; in the prepared frequency distribution of the board surface height, when a detected frequency is a certain prescribed threshold value or higher and a detected value representing the board surface height lies in a range of a standard height plus or minus a prescribed error, then based on the detected value representing the board surface height, correcting the three dimensional profile image signal of the part-mounted board detected by the height detection optical system from an adjacent scanning region adjacent to a desired scanning region; and, based on the corrected three dimensional profile signal, inspecting a state of mounting of parts and jointing on the part-mounted board.

23. A part-mounted board inspection apparatus comprising: a height detection optical system for scanning two-dimensionally a part-mounted board to detect a three dimensional profile image signal from the part-mounted board; a board height detecting and controlling means for preparing a frequency distribution of a board surface height for each of a plurality of desired scanning regions from the three dimensional profile image signal detected by the height detection optical system, and, in the prepared frequency distribution of the board surface height, when a detected frequency is a certain prescribed threshold value or higher and a detected value representing the board surface height lies in a range of a standard height plus or minus a prescribed error, for controlling a distance between the height detection optical system and the part-mounted board based on the detected value representing the board surface height, for detecting the three dimensional profile image signal of the part-mounted board by said height detection optical system from an adjacent scanning region adjacent to a desired scanning region; and an inspecting means for inspecting a state of mounting of parts and jointing on the part-mounted board based on the three dimensional profile image signal detected from said board height detecting and controlling means.

24. A part-mounted board inspection apparatus comprising: a height detection optical system for scanning two-dimensionally a part-mounted board to detect a three dimensional profile image signal from the part-mounted board; a board height detecting and correcting means for preparing a frequency distribution of a board surface height for each of a plurality of desired scanning regions from the three dimensional profile image signal detected by said height detection optical system, and, in the prepared frequency distribution of the board surface height, when a detected frequency is a certain prescribed threshold value or higher and a detected value representing the board surface height lies in a range of a standard height plus or minus a prescribed error, for correcting the three dimensional profile image signal of the part-mounted board detected by said height detection optical system from an adjacent scanning region adjacent to a desired scanning region based on a detected value representing the board surface height; and an inspecting means for inspecting a state of mounting of parts and jointing on the part-mounted board based on the three dimensional profile image signal detected from said board height detecting and correcting means.

25. An automatic focusing method as claimed in claim 1, wherein the stage scanning region is scanned in a plurality of windows, the board surface height is detected in said plurality of windows which are set in the stage scanning region, and the board surface height or inclination is forecasted in a next window from the board surface height already detected in a plurality of windows.

26. An automatic focusing method as claimed in claim 25, wherein, depending on whether a forecast of the board surface height or inclination in said next window is valid or invalid, when histograms of a three dimensional profile signal are calculated for each window, the board surface height of a present window is detected from said corresponding histogram, such that when the difference between said detected board surface height and the focal plane of said height detection optical system is within a certain prescribed range and the detected board height is judged to be valid, the board surface height or inclination in the window to be scanned next is forecasted from the already-detected board surface height in a plurality of windows, including the window detected for a histogram, and the control history of stage height, and when the difference is not in a certain prescribed range and the detected board height is judged to be invalid, the board surface height or inclination in the window to be scanned next is forecasted from the already-detected board height in a plurality of windows, not including said window detected for the histogram.

* * * * *